United States Patent [19]

Witiak et al.

[11] Patent Number: 5,336,796

[45] Date of Patent: Aug. 9, 1994

[54] DIASTEREOMERIC MONO- AND DI-SUBSTITUTED DIAMINO CYCLOHEXANE COMPOUNDS AND THE METHOD OF PREPARATION THEREOF

[75] Inventors: Donald T. Witiak, Mt. Vernon, Ohio; David P. Rotella, State College, Pa.

[73] Assignee: Ohio State University, Columbus, Ohio

[21] Appl. No.: 49,672

[22] Filed: Apr. 16, 1993

Related U.S. Application Data

[62] Division of Ser. No. 882,258, Jul. 7, 1986, Pat. No. 5,206,400.

[51] Int. Cl.$^5$ ............................................. C07F 15/00
[52] U.S. Cl. ................................. 556/137; 556/136
[58] Field of Search ............................... 556/137, 136

[56] References Cited

U.S. PATENT DOCUMENTS

| | | | |
|---|---|---|---|
| 4,968,826 | 11/1990 | Totani et al. | 556/137 |
| 5,041,581 | 8/1991 | Khokar et al. | 556/137 |
| 5,107,007 | 4/1992 | Farrell | 556/137 |
| 5,130,450 | 7/1992 | Kogawa et al. | 556/137 |
| 5,178,876 | 1/1993 | Khokar et al. | 556/137 X |

*Primary Examiner*—Paul F. Shaver
*Attorney, Agent, or Firm*—Emch, Schaffer, Schaub & Porcello

[57] ABSTRACT

One aspect of the present invention relates to a process of making cyclohexane-1,2-di(O)-4,5-di(N) diastereomers which are useful as a synthons for various diastereoisomeric pharmaceutical systems. The present invention also relates to the stereoisomer compounds which are derived from retro-synthetic analysis. In another aspect, the present invention relates to novel antineoplasic Pt(II) complexes derived from the stereoisomers and the processes for making such Pt(II) complexes. Mono- and di-hydroxyl substitution on the cyclohexane ring renders the organoplatinum complex relatively more water soluble, thereby facilitating intravenous administration. The Pt(II) complexes of the present invention are less nephrotoxic than cisplatin and are readily excreted via the kidney due to their enhanced water solubility. In a composition aspect, the present invention encompasses novel pharmaceutical compositions comprising the novel Pt(II) complexes in an amount sufficient to have an antineoplastic effect in an animal or patient.

6 Claims, No Drawings

DIASTEREOMERIC MONO- AND DI-SUBSTITUTED DIAMINO CYCLOHEXANE COMPOUNDS AND THE METHOD OF PREPARATION THEREOF

This is a divisional of copending application Ser. No. 06/882,258 filed on Jul. 7, 1986, now U.S. Pat. No. 5,206,400.

BACKGROUND OF THE INVENTION

The present invention relates generally to diastereomeric mono- and dihydroxylated diamino cyclohexane compounds and the methods for preparing them in a stereocontrolled manner. The invention also relates to the use of such compounds as synthons in the preparation of platinum complexes for such pharmaceutical uses as antitumor agents.

Vicinal, 1,3-, and 1,4-relationships of O and N functions in pharmacologically active compounds are of particular interest in drug design. In particular, appropriately functionalized aminocyclitols of the cyclohexane diol diamine type serve as synthons for cyclic and acyclic compounds. The synthons are useful for mechanism-based stereostructure-activity investigations in numerous biological systems. A synthon is a structural unit within a molecule which is formed and/or assembled by conceivable synthetic operations. These operations refer not to laboratory manipulations, but to structural transformations in the molecular sense. A synthon is an idealized fragment produced by bond disconnection during a retrosynthetic analysis. Synthons also serve as the focal point for the facile elaboration of compounds with a diversity of pharmacological activity. Thus, a single generic synthon provides avenues for entry into a range of biological areas. A number of synthons have been produced from such compounds as carbohydrates and amino acids which permit the implementation of this conceptual strategy in the organic synthesis of cyclic and acyclic compounds.

To be useful for biological investigations, the synthon must provide isomeric compounds since many pharmacological systems display enantio- and diastereo- meric preferences. Incorporation into a pharmacological system of functional substituents which are suitable for conversion into various targets of biological interest is an important factor in selecting a synthon. The functional substituents must be able to impose a high degree of either enantio- or diastereo-meric control during key reactions.

To be most useful, the synthon must be able to strike a positional balance in a particular synthetic scheme, be sufficiently complex in structure, and be available in sufficient quantity so that divergent syntheses may be completed. In addition, synthons useful in medicinal chemistry must be convertible to several biologically different targets, have a wide isomeric pool, and be readily available and facilitate inexpensive preparation.

In particular, cyclohexane diol-diamine types of aminocyclitols serve as synthons and are found in such substances as streptamine, epistreptamine, 2-deoxystreptamine, 2,5- and 2,6-dideoxystreptamine, actinamine and fortamine. While these substances occupy an important place in antimicrobial chemotherapy, the cyclohexane diol-diamines, as a group, have received relatively little attention. Although there are eleven possible regioisomeric cyclohexane diol-diamines 1-11, as shown below, previous synthetic efforts have centered mainly on regioisomers 5-10. Selected diastereomers of the 5-10 compounds have been employed as mutasynthons for the preparation of new antibiotics having altered sensitivity to plasmid- and nonplasmid- mediated bacterial resistance. Also, one stereoisomer, reported in Kuglov et al., *Vesti. Akad. Navak BSSR, Ser. Khing Navuk*, 1981, 5, 66–71, of compound 7 possesses antihypertensive activity.

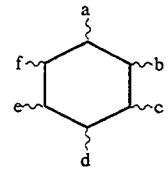

1, a = f = OH, b = c = NH₂, d = e = H
2, a = e = OH, b = c = NH₂, d = f = H
3, a = d = OH, b = c = NH₂, e = f = H
4, a = d = H,  b = c = NH₂, e = f = OH
5, a = e = OH, b = d = NH₂, c = f = H
6, a = c = H,  b = d = NH₂, e = f = OH
7, a = c = OH, b = d = NH₂, e = f = H
8, a = d = OH, b = f = H,   c = e = NH₂
9, a = d = NH₂, b = c= OH, e = f = H
10, a = d = OH, b = e = NH₂, c = f = H
11, a =d = NH₂, b = f = OH, c = e = H

Only certain regioisomers of cyclohexane diol-diamines have been synthesized and biologically investigated for use as synthons. In particular, only the synthesis of derivatives of compound 1 has been performed, as reported in Kresze, G. and Melzer, H., *Justus Liebige Ann. Chemie*, 1874 (1981).

While this cyclohexane diol-diamine nucleus is useful as a synthon, the synthon capabilities embodied in 4 have not been previously investigated, nor has there been any investigation into the use of synthons such as the cyclohexane diol diamine nucleus as a synthon for the synthesis of analogs of the organo platinum antitumor agent, cisdiammin dichloro platinum II (cisplatin). Cisplatin is used for patients with a variety of terminal malignancies. However, the clinical utility of the antitumor agent cisplatin is limited by severe nephrotoxicity where damage is directly correlated with the dosage and ranges from tubular swelling to total necrosis. Other side-effects include ototoxicity leading to high frequency hearing loss and mental confusion. Therefore, while cisplatin has shown to be beneficial in a broad spectrum of antitumor activity, there is a need for continued research for improved congeners of cisplatin with reduced nephrotoxic and emetic effects.

One successor to cisplatin is the dichloro trans-1,2-diaminocyclohexane Pt(II) complex 13a which displays high activity against a broader range of tumors than cisplatin, and a lack of cross resistance without significant nephrotoxicity. However, this compound 13a has a low therapeutic index which imposes dosage limits on the course of therapy. Also, since the 13a compound lacks sufficient aqueous solubility it is very difficult to make pharmaceutical formulations for intravenous administration.

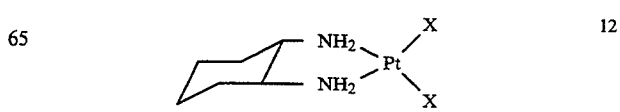

12

-continued

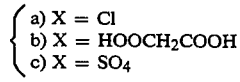

In an effort to overcome these problems, modifications to 12 focus primarily on the chloride leaving groups such as substitution of either malonate, 13b or sulfate, 13c for the chloride ions. The sulfato analog 13c is very water soluble and highly reactive. However, 13c retains a high degree of toxic potential and suffers from stability problems in aqueous formulations as a result of this chemical lability. Bidentate carboxylate ligands, such as malonate 13b are at the other end of the reactivity spectrum. Much higher doses of 13b are needed than would otherwise be employed and such higher doses lead to neurological and otological toxicities as well as significant myelosuppression.

In light of the importance of developing synthons useful in biological investigations, it can readily be appreciated that a need exists for the development of novel synthons which provide isomeric compounds capable of being converted to several biologically active pharmaceutical compounds. There is a need for synthons which are capable of imposing a high degree of enantio and/or diastereomeric control during various key reactions in the synthesis of the pharmaceutical compounds. There is a further need for the development of synthons useful in medicinal chemistry which are readily available and which facilitate inexpensive preparation of the desired pharmaceutical compounds.

It can also readily be appreciated that a need exists for the development of new organoplatinum chemotherapeutic compounds less toxic than the known cisplatin compound which can be readily prepared from synthons capable of imposing diastereomeric control during the synthesis of such chemotherapeutic compounds. There is a further need for organoplatinum compounds which are more active than cisplatin and have a greater spectrum of anti-tumor efficacy than cisplatin. There is another need for organoplatinum compounds which show a wide range of activity and which do not lead to additive toxicity when used alone or in combination with other therapeutic agents.

There is still another need for attractive synthetic routes for the preparation of such synthons and the novel organoplatinum compounds prepared therefrom.

SUMMARY OF THE INVENTION

One aspect of the present invention relates to a process of making cyclohexane-1,2-di(O)-4,5-di(N) diastereomers of 4 which are useful as synthons for various diastereoisomeric pharmaceutical systems. The present invention also relates to the stereoisomer compounds 4 which are derived from retro-synthetic analysis.

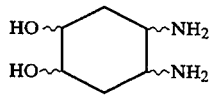

In another aspect, the present invention relates to novel antineoplastic Pt(II) complexes 14 derived from the stereoisomers 4 and the processes for making such Pt(II) complexes 14a, 14b and 14c. Mono- and dihydroxyl substitution on the cyclohexane ring renders the organoplatinum complex relatively more water soluble, thereby facilitating intravenous administration. The Pt(II) complexes 14 of the present invention are less nephrotoxic than cisplatin and are readily excreted via the kidney due to their enhanced water solubility.

In a composition aspect, the present invention encompasses novel pharmaceutical compositions comprising the novel Pt(II) complexes 14a, b and c in an amount sufficient to have antineoplastic effect in an animal or patient.

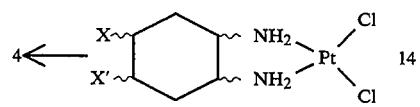

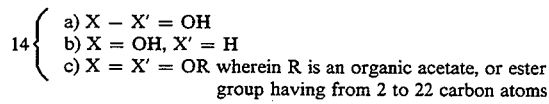

The present invention provides a process for preparing a diastereomeric 1,2-dihydroxylated-4,5-diaminocyclohexane compound which comprises dihydroxylating a bis[benzylcarbamate](Cbz) compound of the formula

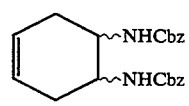

to give the corresponding dihydroxlated benzylcarbamate-protected diamine compound of the formula

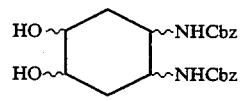

and thereafter liberating, by catalytic hydrogenation, the diastereomeric SP-1,2-dihydroxylated-4,5-diamino cyclohexane compound of the formula

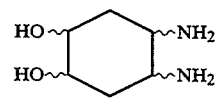

The present invention further provides a process, as described above, wherein the diastereomeric 1,2-dihydroxylated-4,5-diaminocyclohexane synthon compound of the formula 4, immediately after hydrogenation is platinated to form a SP-4,2-dichloro(4,5-dihydroxy-1,2-cyclohexane diamine-N,N')-platinum compound of the formula

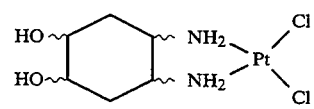

The present invention further provides a process wherein a bis[benzylcarbamate] compound prior to catalytic hydrogenation, is catalytically esterified to give a compound of the formula wherein R is an ester or organic acetate group having from 2 to 22 carbon atoms

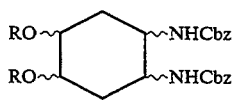

and, following catalytic hydrogenation, platinating the compounds of the formulae 54, 55 and 36 to give the corresponding SP-4,2-dichloro(4,5-di-substituted-oxy-1,2-cyclohexanediamine-N,N')-platinum compound of the formula wherein R is an organic acetate, or ester, group having from 2 to 22 carbon atoms

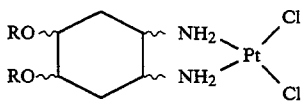

The present invention further provides a process for preparing a diastereomeric SP-4,2-dichloro(4-hydroxy-1,2-cyclohexanediamine-N,N')-platinum compound which comprises the steps of the monohydroxylating the bis[benzylcarbamate](Cbz) compound to give the corresponding monohydroxylated benzylcarbamate-protected diamine compound of the formula:

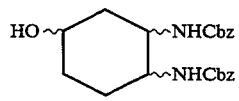

catalytically hydrogenating, and thereafter platinating to give the corresponding diastereomeric SP-4,2-dichloro(4-hydroxy-1,2-cyclohexanediamine N,N')-platinum compound of the formula

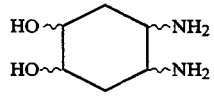

14b

The present invention further provides a diastereomeric 1,2-dihydroxylated-4,5-diaminocyclohexane compound defined according to the generic formula:

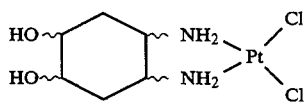

4

The present invention further provides a diastereomeric SP-4,2-dichloro(4,5-dihydroxy-1,2-cyclohexane diamine-N,N')-platinum compound defined according to the generic formula:

14a

The present invention further provides a diastereomeric S,P-4,2-dichloro(4,5-di-substituted-oxy-1,2-cyclohexane diamine-N,N')-platinum compound defined according to the generic formula wherein R is an organic acetate, or ester, group having from 2 to 22 carbon atoms:

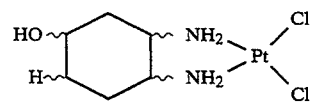

14c

The present invention further provides a diastereomeric SP-4,2-dichloro(4,hydroxy-1,2-cyclohexanediamine-N,N')-platinum compound defined according to the generic formula:

14b

The present invention further provides a pharmaceutical composition comprising at least one of the diastereomeric SP-4,2-dichloro(4,5-dihydroxy-1,2-cyclohexane diamine-N,N')-platinum compounds or pharmaceutically acceptable salts thereof, in an amount sufficient to have an antineoplastic effect in an animal or patient together with at least one pharmaceutically acceptable excipient.

The invention further provides a pharmaceutical composition comprising at least one of the diastereomeric S,P-4,2-dichloro(4,5-diacetyloxy-1,2-cyclohexane diamine-N,N')-platinum compounds or pharmaceutically acceptable salts thereof, in an amount sufficient to have an antineoplastic effect in an animal or patient together with at least one pharmaceutically acceptable excipient.

The invention further provides a pharmaceutical composition comprising at least one of the diastereomeric S,P-4,2-dichloro(4-hydroxy-1,2-cyclohexane diamine-N,N')-platinum compounds or pharmaceutically acceptable salts thereof, in an amount sufficient to have an antineoplastic effect in an animal or patient together with at least one pharmaceutically acceptable excipient.

DETAILED DESCRIPTION OF THE INVENTION

Novel stereocontrolled pathways lead to the six aminocyclitol diastereomers 4a–f which belong to the cyclohexane-1,2-di(O)-4,5-di(N) series of the present invention. The relative stereochemical relationships of the diastereomers 4a–4f are defined as follows:

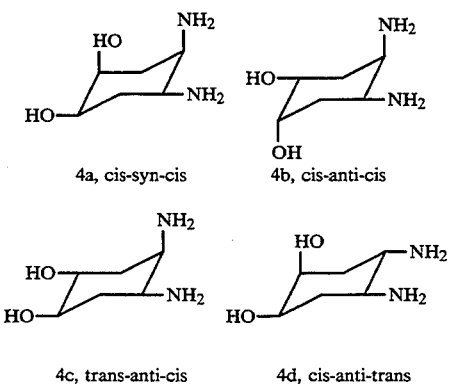

4a, cis-syn-cis     4b, cis-anti-cis 4c, trans-anti-cis     4d, cis-anti-trans

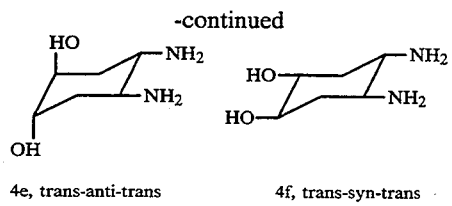

4e, trans-anti-trans     4f, trans-syn-trans

Compounds 4a–4f are named according to IUPAC nomenclature. For convenience, the stereochemical relationships between the hydroxyl and amino groups are described as follows: the "front" hydroxyl function bonded to C-1 (as arbitrarily designated by IUPAC convention) its relationship to the vicinal alcohol is specified as cis or trans (c or t). The orientation of the "C-2" OH group to the 4-amino group is described as syn or anti (s or a) and the vicinal amine stereochemistry follows the cis/trans convention. Proceeding clockwise from the lower left of the molecule, isomer 4a is designated as cis-syn-cis (csc) and 4d as cis-anti-trans (cat), etc.

The generic structure of the cyclohexane diol-diamine stereoisomers 4a–4f of the present invention are attractive synthons because, according to the present invention, all six diastereomers are now available via short stereocontrolled pathways employing readily available reagents. Diastereomers 4a–4f are useful in the preparation of novel hydroxylated organoplatinum complexes 14 for antitumor evaluation. Oxygenation of the diaminocyclohexane ligand provides sites for metabolism and further chemical derivatization to improve the water solubility of the organoplatinum complex. Access to the complete series of the organoplatinum complexes affords a spectrum of agents which show unique stereoisomeric differences in solubility and antineoplastic properties.

The amelioration of toxicity and improving hydrophilicity of organoplatinum complexes is achieved by making modifications on the diamine ligand of the diastereomer synthons 4a–4f of the present invention. Addition of one or more hydroxyl functions to the cyclohexane diamine portion of the organoplatinum complex provides a means by which these improvements are made. The hydroxyl groups serve as sites for chemical derivatization with sugars or dicarboxylic acids to increase aqueous solubility, if the parent system is insufficiently soluble in water. Furthermore, metabolic modification of the drug at the glycol moiety by glucuronidation, sulfate or phosphate formation is another choice by which the hydrophilicity of the complex is improved and toxicity lessened. The following diol-diamine Pt(II) complexes 44–49 are prepared according to one aspect of the present invention:

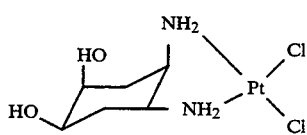

44

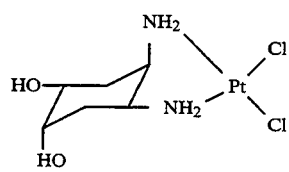

45

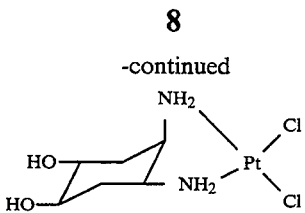

46

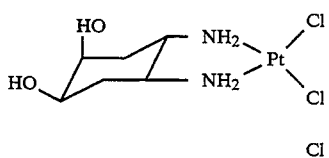

47

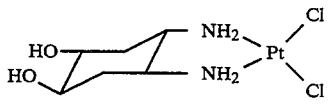

48

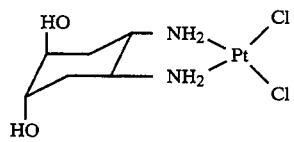

49

In addition, the four stereoisomeric hydroxy-diamine analogs 50–53 derived from an olefinic intermediate in the synthetic sequence serve as additional probes of the stereospecific effects of hydroxyl substitution on the antineoplastic activity of the diaminocyclohexane-Pt nucleus.

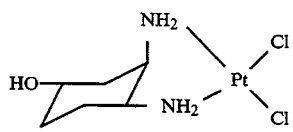

50

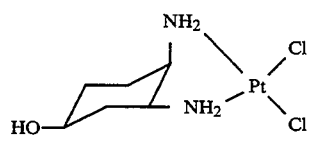

51

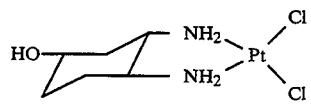

52

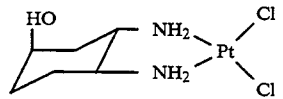

53

Further, three corresponding complexes, 56–58 wherein R is an ester or organic acetate group having from 2 to 22 carbon atoms, serve as additional probes of the stereospecific effects of further substitutions on the antineoplastic activity of the diaminocyclohexane-Pt nucleus.

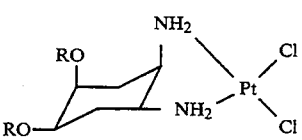

56

-continued

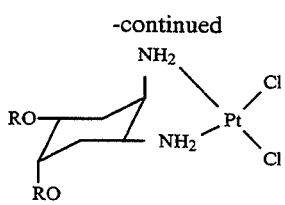
57

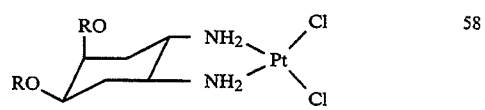
58

The syntheses of the novel compounds of the invention are based upon oxidative manipulation of the suitably protected diaminocyclohex-4-enes 15 and 16. Stereocontrolled glycol formation via mild, inexpensive and readily available reagents provides the target diol diastereomers.

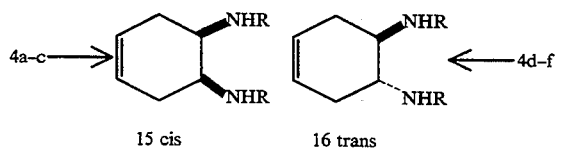

15 cis    16 trans

Stepwise Curtius rearrangement, as reported in Kricheldorf, H. R., Chem. Ber., 1972, 105, 3958–3965, and shown in scheme 1 below, and hydrolysis in situ of the intermediate bis(isocyanate) 19 affords cis-15 .2HCl in 50% overall yield from tetrahydrophthalic anhydride 17. Similarly, bis(acylchloride) 21 is converted to trans-16 2HCl in 59% net yield. Respective bis[benzylcarbamates (Cbz)] 20 and 22 are desired, since subsequent applications of cyclohexane diol-diamines require facile removal without inorganic by-products. Use of 1,2,2,6,6-pentamethylpiperidine (PMP) in aqueous THF provides bis(Cbz) 20 and 22 in excellent yield by recrystallization of the crude reaction mixtures. Excess benzyl alcohol addition to the Curtius intermediate bis(isocyanates) affords the respective isomers 20 and 22 in approximately 30% yield. Additional chromatographic procedures are required to separate desired materials from complex mixtures.

SCHEME 1<sup>a</sup>

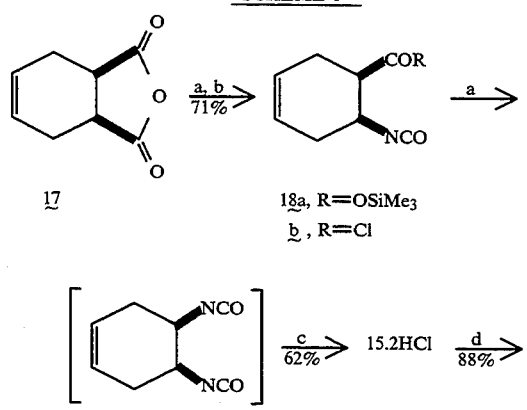

-continued
SCHEME 1<sup>a</sup>

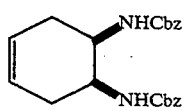
20

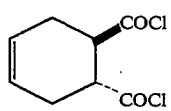
21

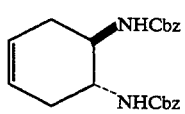
22

<sup>a</sup>a = Me₃SiN₃, dioxane, ;
b = SOCl₂, cat. DMF, CCl₄, ;
c = con. HCl, 35° C.;
d = CbzCl, 1,2,2,6,6-pentamethylpiperidine (PMP), aq. THF. 0° C.

Catalytic osmylation of trans-22 affords cis-anti-trans 23 (98%) which serves as a stable source of 4d as shown in Scheme 2 below. The ¹H NMR spectrum differs from the spectra for the remaining five diastereomers as shown in Table 1 below. Exclusive formation of 23 from 22 during osmylation from either side of the Pi system is a function of the 2-fold axis of symmetry in the product. Similar osmylation of cis-22 at room temperature for 16 h proceeds with little stereocontrol, and a 90% yield of a 1.3:1.0 ratio of 24 to the sterically more congested isomer 25 is obtained. At −20° C. (5 da) a modest increase (2.1:1.0, respectively) in stereoselectivity is achieved. Unexpectedly, these results indicate that the pseudoaxial carbamate presents only a minor degree of steric impedence to OsO₄ for approach to the Pi system.

SCHEME 2<sup>a</sup>

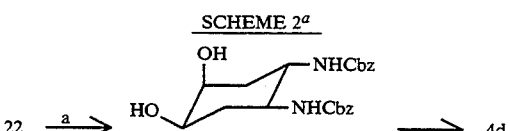

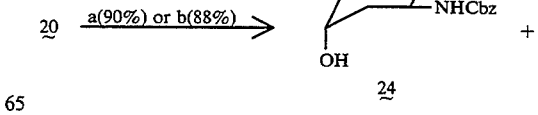

For a 1.3
For b 2.1

-continued
SCHEME 2[a]

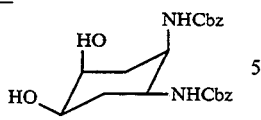

25

[a] a = N-methylmorpholine-N-oxide (NMO), cat. OsO$_4$, aq. acetone-t-BuOH, rt, 16h;
b = NMO, cat. OsO$_4$, aq. acetone-t-BuOH, −20° C., 5 days.

TABLE 1.

500 MHz $^1$H NMR Resonance Signals (δ) Assignments for cyclohexane diol-diamines diastereomers 4a–f.

| compd. | H$_1$ | H$_2$ | H$_{3a}$ | H$_{3e}$ | H$_4$ | H$_5$ | H$_{6a}$ | H$_{6a}$ |
|---|---|---|---|---|---|---|---|---|
| 4a | 3.75–3.95 | | 1.82–1.98 | 1.98–2.20 | 3.65–3.75 | | 1.82–1.98 | 1.98–2.20 |
| 4b | 3.86–3.96 | | 1.88–1.96 | 2.00–2.08 | 3.80–3.86 | | 1.88–1.96 | 2.00–2.08 |
| 4c | 3.72 | 3.83 | 1.82 | 2.07–2.16 | 3.80 | 3.67 | 1.86 | 2.07–2.16 |
| 4d | 3.73 | 3.95 | 1.68 | 2.22 | 3.52 | 3.42 | 1.82 | 2.02 |
| 4e | 3.52–3.60 | | 1.55–1.63 | 2.28–2.34 | 3.43–3.50 | | 1.55–1.63 | 2.28–2.34 |
| 4f | 3.89–3.93 | | 1.95–2.02 | 2.02–2.10 | 3.60–3.64 | | 1.95–2.02 | 3.02–2.10 |

[a] Compounds 4a–f are numbered starting with the carbon bearing hydroxyl group as No. 1 in the lower left part of the ring.

Notable differences in the 500 MHz $^1$H spectra of the cis-anti-cis 24 and cis-syn-cis 25 compounds support the diastereomeric assignments proposed on the basis of mechanistic principles. At identical concentrations in acetone-d$_6$ solution, the NH (6.45 δ) and OH (4.14 δ) proton resonance signals in 25 are downfield to those of 24 (6.27 and 3.70 δ, respectively). Intramolecular hydrogen bonding owing to the 1,3-diaxial relationship of OH and NH functions in 25 (and in its flip conformation) account for the downfield shift. Furthermore, the NH protons in 25 exchange with D$_2$O at a much faster rate (15 min) than those in 24 (exchange not observable after 30 min.). Hydroxyl proton exchange with D$_2$O proceeds equally rapidly for both isomers. Confirmation of the relative stereochemical assignments for these isomers is provided by X-ray analysis of the dichloro Pt(II) complex of 4a derived from 25 which clearly showed the cis-syn-cis arrangement of OH and NH$_2$ functions.

Epoxidation of olefins 20 and 22 is carried out at room temperature with two equivalents of freshly purified m-chloroperbenzoic acid (MCPBA) and each affords a single epoxide 26 (86%) and 29 (73%), respectively, as shown in Scheme 3 below. Lower oxirane yields result when commercially available technical grade or less peracid (1.2–1.5 equivalents) is employed. Unlike 29, which has a C$_2$ axis of symmetry and whose 500 MHz $^1$H NMR spectrum is first order, 26 displays a deceptively simple spectrum with insufficiently resolved two-proton multiplet resonance signals at δ 3.85 (H-3 and H-4), 3.2 (H-1 and H-6) and 2.35 (H2e and H5e). As such, the oxirane configuration of 26 is determined chemically.

NaBH$_4$ reduction (or use of LiBH$_4$ in THF) of 26 affords a single alcohol 27 (72%) identical in all respects to the major diastereomer [3.5 (27):1.0 (28)] resulting from exposure of 20 to excess B$_2$H$_6$/alkaline peroxide, as shown in Scheme 3 below. Since diborane is known to hydroborate the sterically most accessible face of a Pi system, the major component should be 27. Thus, delivery of oxygen by MCPBA to 20 is mainly influenced by steric rather than electronic factors.

SCHEME 3[a]

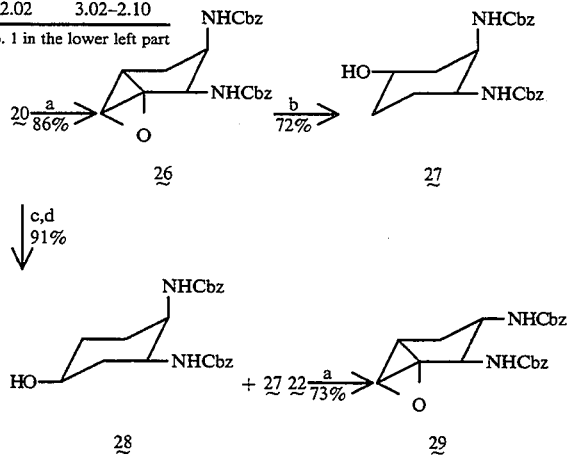

[a] a = MCPBA, CH$_2$Cl$_2$, rt;
b = NaBH$_4$, t-BuOH, MeOH, ;
c = B$_2$H$_6$, dry THF, 0° C., 6h; d = NaOH, 30% H$_2$O$_2$, −20° C., warm to rt over 3h.

Acid-catalyzed hydrolysis, as shown in Scheme 4 below, of epoxides 26 and 29 at room temperature afford trans-anti-cis 30 (73%) and trans-anti-trans 31 (69%), respectively, which in turn serve as stable precursors to diol-diamines 4c and 4e. Formation of 31 from 29 is accompanied by bicyclo [3.3.1] oxazolidone 32 (16%). The ratio of 31:32 is unchanged at temperatures between 0°–65° C. Treatment of 29 with glacial HOAc in the presence or absence of NaOAc or with H$_2$O$_2$/HCO$_2$H mainly affords 32 and traces 31.

SCHEME 4[a]

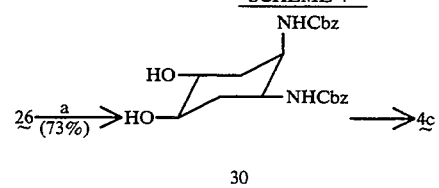

-continued
SCHEME 4[a]

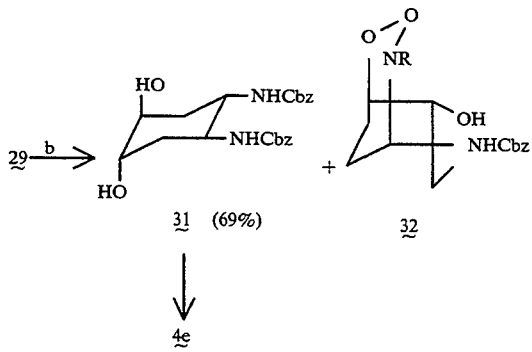

31 (69%)  32

↓

4e

[a]a = 1% aqueous H$_2$SO$_4$, acetone or THF, rt, 6h;
b = 1% aqueous H$_2$SO$_4$, actone or THF, rt, 2h.

Formation of the bicyclo [3.3.1] system 32 via proposed intermediate 33 results from preferred anchimerically assisted proton catalyzed diaxial opening of epoxide 29. This pathway should be favored over formation of the bicyclo [3.2.2] skelton 34 wherein the carbocyclic ring is forced into a diaxially substituted boat conformation even though transition states leading to each are allowed processes. However, $^1$H NMR double resonance experiments do not distinguish between these two possibilities. Correlation of long-range H-C couplings (by COLOC) carried out on the hydrogenolysis (debenzylated) compound clearly establishes structure 32 as the product. Correlation between the proton resonance signals at δ 3.78 and 4.55 with the carbonyl resonance signal at δ 156 indicates that the proton signals are attributable to H-5 and H-1, respectively. Observation of a similar 3-bond J$_{C-H}$ correlation between the resonance signals for H-1 and C-5 (δ 46) and H-5 and C-1 (δ 75) can only take place in the debenzylated bicyclo [3.3.1] product of 32.

Facilitation of hydrolysis by a neighboring axial carbamate functionality as in 29 is not possible during oxirane hydrolysis of 26. Whereas cleavage of 29 is complete after two hours at room temperature, 26 requires six hours and no bicyclic product formed.

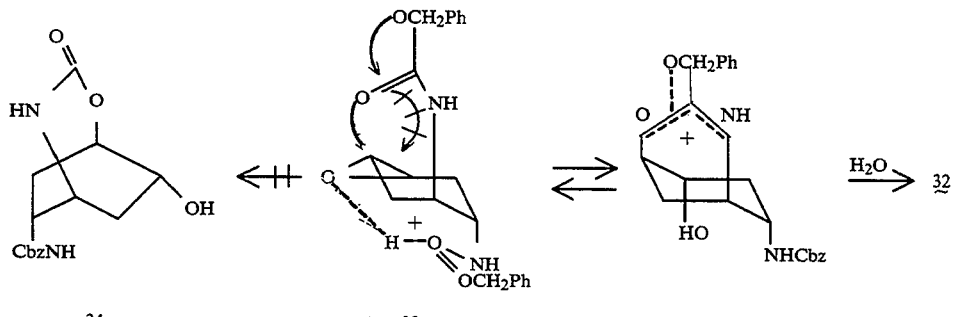

34      29      33

32 can not be converted to trans-syn-trans cyclohexane diol-diamine 4f under a variety of conditions. The synthesis for 4f is achieved from cis-anti-trans 23. Regioselective monoacetylation (1.1 equivalents of Ac$_2$O with 4-dimethylaminopyridine as catalyst) in THF at −25° C. furnished 35 (73%) contaminated with diacetate 36 (8%) (independently prepared in 92% yield using excess Ac$_2$O at room temperature). Anticipated equatorial acetylation in 35 is in agreement with $^1$H NMR analysis confirming the relative downfield shift from the H-4 or H-5 resonance signals in 23 of the H$_4$ axial proton (δ 5.10). Decoupling of equatorial H-5 (α to the OH group in 35) reveals the requisite axial-equatorial and diaxial coupling constants of 5 and 12 Hz between H-4 and the C-3 methylene protons. Jones oxidation of 35 affords keto acetate 37 (87%). Reduction (NaBH$_4$) and acetylation affords diacetates 38 (65%) and 36 (9%) separable by chromatography. Deacetylation (MeOH, K$_2$CO$_3$) affords 39, a stable precursor to the cyclohexane diol-diamine 4f.

The cyclohexane diol-diamines 4a-f form hygroscopic salts (HCl or dicarboxylates). Free amines are characterized by 500 MHz $^1$H NMR spectroscopy and/or by conversion in situ to their Pt(II) complexes following treatment with K$_2$PtCl$_4$.

SCHEME 5[a]

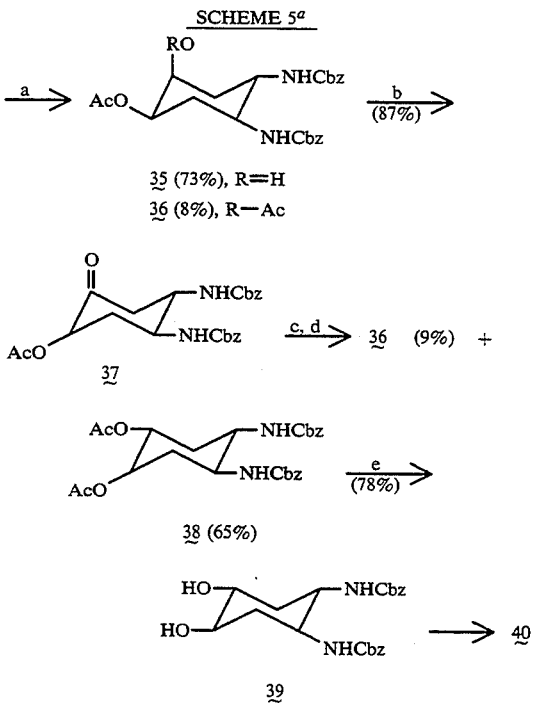

[a]a = 1.1 eq. Ac$_2$O, 4-dimethylaminopyridine (DMAP), THF, −25° C., 24h;
b = 2.5M Cr[+6], acetone, ice-bath, 2h;
c = NaBH$_4$, THF, EtOH, −78° C., 1h;
d = Ac$_2$O, DMAP, Et$_3$N, rt, 1h;
e = K$_2$CO$_3$, MeOH, Δ 1h, rt, 1.5h.

The synthesis of the four hydroxy-diastereomers 27-28 and 40-41 from olefins 20 and 22 is achieved nonstereoselectively using diborane. Three molar equivalents of the reagent are required for complete hydroboration of the starting materials. In the case of cis-20, a 3:1 ratio of alcohols 27 and 28 is obtained in 91% yield. The same ratio of products results when the reaction is carried out at room temperature or at 0° C. or with up to five molar equivalents of diborane. Trans olefin 22 provides a 1.4:1 ratio of alcohols 40 and 41 in 78% yield when treated with diborane under similar conditions.

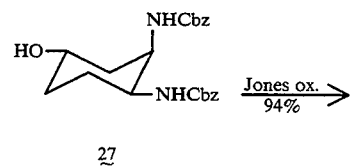

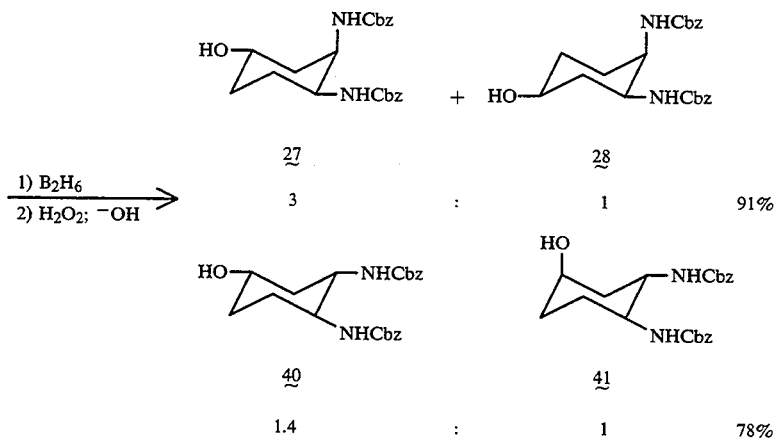

Stereoselective reduction of the ketones derived from these alcohols is as follows: trans diamino-ketone 42 is prepared in 87% yield by Jones oxidation of a diastereomeric mixture of 40 and 41. Treatment of 42 with 1.3 molar equivalents of NaBH$_4$ at −20° C. gives primarily the expected equatorial alcohol 40 in 65% yield, accompanied by only a small amount of 41. This ratio is improved by performing the reaction at −78° C. Conversely, exposure of 42 at low temperature (−78° C.) to 1.2 equivalents of K-Selectride in THF furnishes a 20:1 ratio of axial:equatorial alcohols in 86% yield. These results confirm the structural assignments made as a result of the hydroboration-oxidation of 22.

In β-substituted cyclohexanones, the usual stereochemical outcome of NaBH$_4$ reductions is often reversed. The presence of an axial β-substituent leads to predominant equatorial delivery of hydride as opposed to normal axial attack. The eventual result of this reduction indicates that the axial nitrogen substituent does not Cis diamino-ketone 43 is prepared in 94% yield by Jones oxidation of alcohol 27. Unlike 42, two conformations are available to 43 which differ only slightly in energy at room temperature.

coordinate with the reducing agent facilitating an axial vector for delivery of hydride from the sterically more hindered side of 43.

The diastereomeric outcome is dependent upon temperature, and amount and mode of addition of the reducing agent. Good results are achieved at −78° C. using 0.6 molar equivalents of NaBH4. At higher temperatures or when the reducing agent is added all at once, less stereoselection is observed. The results of these experiments are tabulated in Table II below.

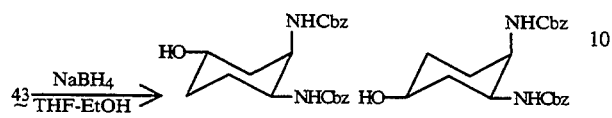

TABLE II

Effect of temperature, amount of NaBH4, and mode of addition on reduction of ketone 43.

| Temp. | Mode of Addition | Molar Equiv. NaBH4 | Ratio of 28:27 |
|---|---|---|---|
| −78° | divided | 0.6 | 18:1 |
| 0° C. | divided | 0.6 | 3:1 |
| 25° C. | divided | 0.6 | 1.5:1 |
| −78° | 1 portion | 0.6 | 4:1 |
| 0° C. | 1 portion | 0.6 | 1.8:1 |
| 25° C. | 1 portion | 0.6 | 1.2:1 |
| −78° | divided | 1 | 9:1 |
| 0° C. | divided | 1 | 1.5:1 |
| 25° C. | divided | 1 | 1.2:1 |

Treatment of ketone 43 with a slight excess of K-Selectride at −78° C. in THF leads to the formation of alcohols 28 and 27 in a ratio of 1.3:1. Alcohol 28 is the product arising from preferred equatorial attack on the predicted favored conformation, while the less sterically hindered 27 arises from the less favorable 43b, indicating that even at low temperature, substantial amounts of this conformer are present.

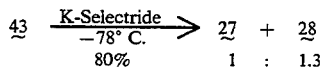

The six dihydroxy diamines 4a–4a and four diamino alcohols derived from 27–28 and 40–41 are prepared by catalytic hydrogenation of the protected species in methanol at 20 psi for two hours. NMR analysis at 90 or 270 MHz shows that each isomer is generated in yields of at least 90%.

Attempted isolation of the diol-diamines as salts (HCl, oxalate, succinate, citrate) is frustrated by their hygroscopic nature while the free bases darkened on standing. Therefore, the platination of all diamines is carried out immediately following hydrogenation, as shown in Tables III and IV below.

TABLE III

HO—[cyclohexane]—NHCbz, HO—[cyclohexane]—NHCbz  1) H2/10%Pd-C  2) K2PtCl4;H2O →

HO—[cyclohexane]—NH2, HO—[cyclohexane]—NH2—Pt(Cl)(Cl)

| | Pt complex | % yield | H2O hydration |
|---|---|---|---|
| 23, 24, 25 | 45 cac | 43 | 1 |

TABLE III-continued

HO—[cyclohexane]—NHCbz, HO—[cyclohexane]—NHCbz  1) H2/10%Pd-C  2) K2PtCl4;H2O →

HO—[cyclohexane]—NH2, HO—[cyclohexane]—NH2—Pt(Cl)(Cl)

| | Pt complex | % yield | H2O hydration |
|---|---|---|---|
| 30, 31, 39 | 44 csc | 37 | 1 |
| | 46 tac | ? | ? |
| | 47 cat | 73 | 1 |
| | 48 tst | 61 | 1 |
| | 49 tat | <5 | — |

TABLE IV

HO—[cyclohexane]—NHCbz, NHCbz  as above →

HO—[cyclohexane]—NH2, NH2—Pt(Cl)(Cl)

| | Pt complex | % yield | H2O hydration |
|---|---|---|---|
| 27–28 | 50 ac | 37 | — |
| 40–41 | 51 sc | 37 | — |
| | 52 | 65 | ½ |
| | 53 at | 48 | 1 |

Platinum complexes formation is carried out according to the method of Connors, et al., *Chem-Biol. Interact.*, 5,415 (1972). After standing at room temperature for 24 hours, the precipitate is collected by filtration. Precipitation of the complex is observed within one to two hours for the trans analogs. In contrast, the cis derivatives often require five to six hours for noticeable complex formation. The diol-diamine complexes 44, 45, and 46 and hydroxy-diamine complex 53 co-crystallize with one mole of water, as shown by elemental analysis. The X-ray structure of 44 shows the water to be bound between the two hydroxyl groups.

Corresponding diacetates of the diols 23, 25 and 24 are prepared and serve as potential prodrugs for the diol-diamine complexes. These diacetate complexes 56–58 are synthesized as shown in Table V below.

TABLE V

20 —[cyclohexane]—NHCbz, NHCbz  1) OsO4; NMO  2) Ac2O; DMAP →  80% net

54: AcO—[cyclohexane]—NHCbz, AcO—NHCbz  +  55: AcO—[cyclohexane]—NHCbz, AcO—NHCbz

TABLE V-continued

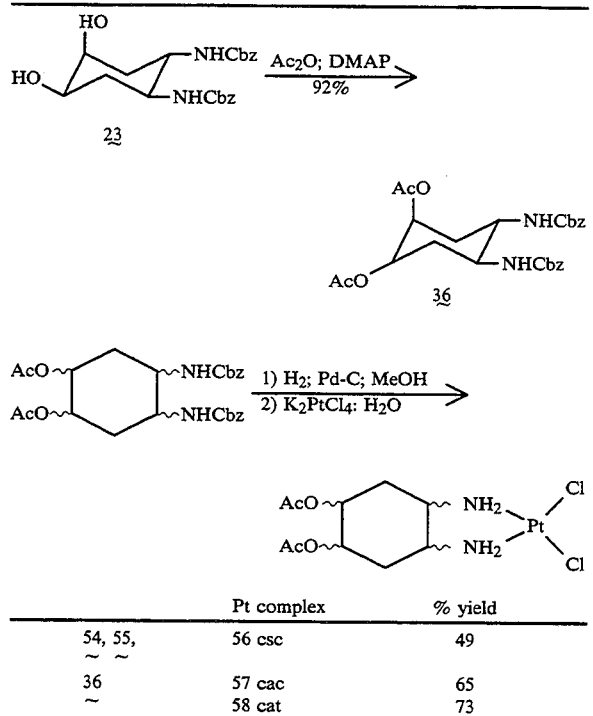

| | Pt complex | % yield |
|---|---|---|
| 54, 55, | 56 csc | 49 |
| 36 | 57 cac | 65 |
| | 58 cat | 73 |

The compounds of the present invention and their salts can be used as pharmaceuticals. Among other things, they have antineoplastic activity and are suitable for inhibiting or preventing cell division in neoplasms. They have enhanced water solubility allowing for facile excretion via the kidney and thus also have reduced nephrotoxicity. They are useful, for example, as a chemotherapeutic alternative to the drug cisplatin in the treatment of various neoplasms.

The antineoplastic activity of the compounds of the present invention was determined using the following procedure: Female DBA/2 and DFA$_1$, mice were obtained from Harlan Labs, Indianapolis, Ind. The mice were housed in gang stainless steel cages in environmentally controlled animal facilities and fed Purina Mouse Chow #5015. Water and food were available ad libitum and all mice were allowed at least 1 week for adaptation to their surroundings before being assigned to a study.

Antitumor experiments were conducted against P388 and/or L1210 leukemias using the experimental protocols developed by the National Cancer Institute (NCI). P388 and L1210 tumors were maintained by continuous passage in the DBA/2 mice. On day 0, ascitic fluid was removed from the peritoneum of a DBA/2 mouse, diluted with Hank's balanced salt solution, cell concentration determined on a Coulter Counter (Model MHR) and $10^6$ P388 cells or $10^5$ L1210 cells were implanted intraperitoneally (0.2 ml) into CDF$_1$ recipient test mice.

After the mice were weighed and implanted with tumor, they were randomly distributed into treatment groups of 7 animals each. Drugs were administered in a single dose. Drugs were evaluated by median survival time (MST). Percent treated to control (T/C) were calculated for each group according to the NCI protocols. Dosing solutions were prepared by dissolution of drug into 0.9% physiological saline or 0.3% Klucel in sterile water.

Over a dosage range of 5 mg/kg to 40 mg/kg, the cis-anti-cis complex 45 displays significant activity as shown in the examples below. At 40 mg/kg 45 has a T/C of 157 while the cis-syn-cis diastereomer shows somewhat less antitumor effects. The trans diamine isomer 47 is toxic at doses above 20 mg/kg. The Pt complex 46 derived from the trans-anti-cis diol also demonstrates antineoplastic activity when given in crude form at a dose as low as 20 mg/kg.

The following examples illustrate the biological antitumor activity of the platinum (II) complex compounds provided by the present invention. All compounds are injected intraperitoneally on a day one schedule. The toxicity levels are defined as toxic if T/C<85. The toxicity levels are defined as active if T/C>120 for the test system P388, and T/C>125 for the test system L1210.

| Compound No. | Test System | mg/kg Dose | MST | T/C |
|---|---|---|---|---|
| | Example A | | | |
| 45 | P388 | 40 | 16.50 | 157 |
| | | 20 | 14.00 | 133 |
| | | 10 | 12.50 | 119 |
| | | 5 | 11.83 | 113 |
| | Example B | | | |
| 47 | P388 | 40 | 3.00 | 29 |
| | | 20 | 4.50 | 43 |
| | | 10 | 12.83 | 122 |
| | | 5 | 12.50 | 119 |
| | Example C | | | |
| 44 | P388 | 40 | 14.50 | 138 |
| | | 20 | 12.00 | 114 |
| | | 10 | 12.50 | 119 |
| | | 5 | 11.17 | 106 |
| | Example D | | | |
| 56 | P388 | 40 | 11.3 | 103 |
| | | 20 | 11.3 | 103 |
| | | 10 | 11.1 | 101 |
| | | 5 | 11.0 | 100 |
| | Example E | | | |
| 58 | P388 | 40 | 12.17 | 111 |
| | | 20 | 12.0 | 109 |
| | | 10 | 11.5 | 105 |
| | | 5 | 10.85 | 99 |
| | Example F | | | |
| 57 | P388 | 40 | 11.25 | 102 |
| | | 20 | 11.0 | 100 |
| | | 10 | 11.1 | 101 |
| | | 5 | 10.5 | 95 |
| | Example G | | | |
| 46 | P388 | 80 | 14.5 | 141 |
| | | 60 | 16.0 | 155 |
| | | 40 | 13.8 | 134 |
| | | 20 | 14.0 | 136 |
| | | 10 | 12.5 | 121 |
| | Example H | | | |
| 50 | P388 | 80 | 4.2 | 42 |
| | | 40 | 8.5 | 86 |
| | | 20 | 16.5 | 168 |
| | | 10 | 15.2 | 154 |
| | Example I | | | |
| 51 | P388 | 80 | 13.5 | 137 |
| | | 40 | 18.0 | 183 |
| | | 20 | 15.0 | 153 |
| | | 10 | 13.8 | 141 |
| | Example J | | | |
| 52 | P388 | 80 | 2.2 | 22 |
| | | 40 | 3.2 | 32 |
| | | 20 | 3.3 | 34 |
| | | 10 | 15.8 | 161 |
| | Example K | | | |
| 52 | L1210 | 20 | 4.0 | 50 |
| | | 10 | 5.5 | 69 |
| | | 5 | 11.5 | 144 |
| | | 2.5 | 10.5 | 131 |

-continued

| Compound No. | Test System | mg/kg Dose | MST | T/C |
|---|---|---|---|---|
| | Example L | | | |
| 53 | P388 | 80 | 2.2 | 22 |
| | | 40 | 5.0 | 51 |
| | | 20 | 14.5 | 147 |
| | | 10 | 16.5 | 168 |
| | Example M | | | |
| 53 | L1210 | 20 | 7.5 | 94 |
| | | 10 | 12.5 | 156 |
| | | 5 | 12.5 | 156 |
| | | 2.5 | 10.5 | 131 |
| | Example N | | | |
| 48 | P388 | 40 | 6.00 | 55 |
| | | 20 | 10.83 | 98 |
| | | 10 | 6.00 | 55 |
| | | 5 | 12.50 | 137 |
| | | 2.5 | 12.50 | 137 |
| | Example O | | | |
| cisplatin | P388 | 6 | 24.5 | 249 |
| | | 3 | 18.5 | 188 |
| | | 1.5 | 15.5 | 158 |
| | Example P | | | |
| cisplatin | L1210 | 6 | 18.5 | 180 |
| | | 3 | 18.2 | 176 |
| | | 1.5 | 16.0 | 155 |

The compounds of the present invention and their salts can be used as medicaments; for example, in the form of pharmaceutical preparations which contain them in association with a compatible pharmaceutical excipient or carrier material. The carrier material can be an organic or inorganic inert carrier material suitable for enteral or parenteral administration such as, for example, water or saline solutions. The pharmaceutical preparations can be made up in a liquid form (e.g. as solutions, suspensions or emulsions). The pharmaceutical preparations may be sterilized and/or may contain adjuvants such as preserving, stabilizing, wetting or emulsifying agents, salts for varying the osmotic pressure or buffers. They can also contain still other therapeutically valuable substances.

The medicaments can be produced in a manner known per se by mixing a compound of the present invention or a salt thereof with a non-toxic, inert, liquid carrier material customary per se in such preparations and suitable for therapeutic administration (e.g. the aforementioned carrier materials) and, if desired, bringing the mixture into the desired dosage form.

The following examples illustrate the processes provided by the present invention: Melting points were determined in open capillaries with a Thomas-Hoover Uni-Melt apparatus and are uncorrected. Infrared spectra were recorded with a Beckman model 4230 spectrophotometer. Nuclear magnetic resonance spectra were recorded using either a Bruker WP-80, HX-90E, 300 MHz or 500 MHz spectrometer. TMS ($CDCl_3$, DMSO, acetone or pyridine) or TSP ($D_2O$) were used as internal standards. Chemical shifts are reported on the scale with peak multiplicities: s, singlet; d, doublet; t, triplet; q, quartet; m, multiplet; dd, doublet of doublets; dt, doublet of triplets. THF was freshly distilled from Na/benzophenone ketyl. Dioxane was distilled first from $CaH_2$ then from Na/benzophenone ketyl. Elemental analyses were performed by Galbraith Laboratories, Inc., Knoxville, Tenn.

EXAMPLE 1

Diastereomeric 1,2-Dihydroxy-3,4-diaminocyclohexanes 4a–f. Deprotection of the respective Cbz-protected diol-diamines. The respective Cbz-protected diamines (100 mg; 0.242 mmol; 23→4d, 24→4b, 25→4a, 30→4c, 31→4e, 39→4f are dissolved in 5 ml of MeOH. Catalyst (10% Pd/C; 20 mg) is added and the bottle alternatively evacuated ($H_2O$ aspirator) and refilled to 20 psi with $H_2$ five times. The suspension is shaken under 20 psi for 2 h. Following filtration (Celite) the colorless filtrate is concentrated in vacuo routinely affording 90% of the free diamines 4a–f whose NMR spectra are recorded in Table V below.

EXAMPLE 2 cis-4-cyclohexene-1,2-diamine Dihydrochloride (15 2HCl). Acid chloride 18b (12.61 g, 68 mmol) is dissolved in 40 ml of dry dioxane under argon in an oven-dried 250 ml round bottom flask. $TMSN_3$ (11.03 g; 95 mmol) is added at room temperature by pipette to the stirred solution which is subsequently heated to 80°–85° C. in an oil bath. $N_2$ evolution begins within 5–10 min and continues for 20–30 min. The reaction is cooled to 35°–40° C. and diluted with 24 ml of $Me_2CO$. Concentrated HCl (17 ml) is added cautiously through the top of the condenser. Stirring is continued until $CO_2$ formation ceased (approximately 30 min). The precipitate is filtered and washed with $Me_2CO$ and $Et_2O$ providing 7.5 g (60%) of the diamine salt as a white powder mp 255°–265° C. IR (KBr) 2800 and 1460 $cm^{-1}$; NMR (90 MHz, $CDCl_3$) $\delta$ 5.62 (deceptively t, 2H, olefinic), 3.75–3.9 (m, 2H, methines), 2.0–2.6 (m, 4H, methylenes). Anal. calc for $C_6H_{14}N_2Cl_2$: C, 38.93; H, 7.62; N, 15.13; Cl, 38.31. Found: C, 39.08; H, 7.44; N, 15.12; Cl, 38.00.

EXAMPLE 3 trans-4-cyclohexene-1,2-diamine Dihydrochloride (16 2HCl). Trans bis(acid chloride) 21 (4.7 g, 23 mmol) is dissolved in 10 ml of dry dioxane under argon in an oven dried 50 ml round bottom flask. $Me_3SiN_3$ (5.85 g; 50 mmol) is added by pipette at room temperature. The flask is immersed in an oil bath preheated to 80° C. Vigorous $N_2$ evolution begins within 10 min after which time the heating bath is removed. When $N_2$ evolution subsides, the orange solution is reheated for ca. 10 min to 80° C. to ensure completion of the rearrangement. The reaction is cooled to 35°–40° C. and diluted with 15 ml of $Me_2CO$ followed by cautious addition of 7 ml of conc. HCl. $CO_2$ evolves immediately, and vigorous stirring is continued until gas generation ceases. The precipitate is collected by filtration and washed with $Me_2CO$ and $Et_2O$ affording 2.6 g (61%) of white powder, mp>280° C.; lit.[25] mp>320° C. IR (KBr) 2820, 1600 and 1515 $cm^{-1}$; NMR (90 MHz, $D_2O$ $\delta$ 5.6–5.7 (m, 2H, olefinic), 3.6–3.8 (m, 2H, methines), 2.0–2.7 (m, 4H, methylenes). Anal. calc for $C_6H_{14}N_2Cl_2$: C, 38.93; H, 7.62; N, 15.13; Cl, 38.31. Found: C, 38.67; H, 7.42; N, 15.22; Cl, 37.34.

EXAMPLE 4 cis-3-cyclohexene-1-carboxylic acid-6-isocyanato-trimethylsilylester (18a) is prepared according to the method of Kricheldorf, H. R., Chem Ber., 1972, 105, pp. 3958–3965. cis-1,2,3,6-tetrahydrophthalic anhydride (Aldrich, recrystallized from toluene, 15.0 g; 99 mmol) is dissolved in 90 ml of dry dioxane under argon in an oven-dried 250 ml round bottom flask. Trimethylsilylazide ($TMSN_3$, 16.0 g; 138 mmol) is added by pipette to the stirred solution held at room temperature. The gently stirring solution is immersed in an oil bath preheated to 80°–85° C. $N_2$ evolution ceases after 30–45 min. The solution is cooled to 35°–40° C. and concentrated in vacuo (bath temp<35° C.) to a slightly yellow oil that is purified by distillation under reduced pressure to furnish 19.36 g (82%) of a colorless liquid bp 80°–84° C. (0.4 torr); lit.[26] bp 82°–84° C. (0.4 torr). IR (neat) 2250 and 1720 cm$^{-1}$. NMR (90 MHz, CDCl$_3$) δ 5.5–5.59 (m, 2H, olefinic), 4.2–4.3 (m, 1H, H-6), 2.5–2.8 (m, 1H, H-1), 2.3–2.5 (m, 4H, methylenes) and 0.3 (s, 9H, SiMe$_3$).

EXAMPLE 5 cis-3-cyclohexene-1-carbonyl chloride-6-isocyanate (18b) is prepared by a modification of the method of Kricheldorf, supra, wherein use of a catalytic amount of DMF provides an improved yield at lower temperature: Trimethylsilyl ester 18a (19.36 g; 81 mmol) is dissolved in 40 ml of CCl$_4$. DMF (10 drops) is added followed by freshly distilled SOCl$_2$ (15.18 g; 113 mmol). The reaction mixture is heated to 40°–50° C. in an oil bath. Gas evolution begins within 5–10 min. The reaction is maintained at approximately 50° C. until the infrared absorption at 1720 cm$^{-1}$ (ester) has disappeared (30–45 min). The solution is cooled to room temperature and concentrated in vacuo to a viscous yellow liquid that is distilled under reduced pressure to furnish 12.61 g (84%) of 18b as a colorless liquid, bp 60°–62° C. (0.15 torr); lit.[26] bp 70°–72° C. (0.2 torr). IR (neat) 2260 and 1790 cm$^{-1}$; NMR (90 MHz, CDCl$_3$) δ 5.5–5.9 (m, 2H, olefinic), 4.4–4.5 (m, 1H, H-6), 3.0–3.2 (m, 1H, H-1), 2.4–2.6 (m, 4H, methylenes). This compound is used immediately for the next reaction.

EXAMPLE 6

Bis(phenylmethyl) cis-4-cyclohexene-1,2-diyl-bis(carbamate) (20). Dihydrochloride 15 2HCl (2.35 g; 13 mmol) is dissolved in 40 ml of THF and 5.0 ml of distilled H$_2$O and cooled in an ice bath. 1,2,2,6,6-Pentamethylpiperidine (PMP; 7.87 g; 58 mmol) is added by pipette. After 10 min, a cold (0° C.) solution of benzyl chloroformate (4.34 g; 25 mmol) in 10 ml of THF is added dropwise over 15 min. Vigorous stirring is maintained for 1 h at ice bath temperature. The reaction is diluted with 100 ml of EtOAc and washed with 3×10 ml of 10% HCl solution. The acidic aqueous layer is back-extracted with 3×20 ml of EtOAc. The combined organic layers are washed with 3×25 ml of brine, dried (MgSO$_4$) and concentrated in vacuo affording a viscous, faintly yellow oil which is purified by flash chromatography (pet ether:EtOAc 3:1) providing the bis-carbamate 20 as a thick colorless liquid. The liquid is induced to solidify when treated with Et$_2$O:hexane affording 4.25 g (88%) of a white powder mp 80°–81° C. which resisted further recrystallization. IR (KBr) 3380, 3360, 1720 and 1680 cm$^{-1}$; NMR (90 MHz, CDCl$_3$) δ 7.34 (s, 10H, aromatic), 5.6 (m, 2H olefinic), 5.2–5.4 (m, 2H, NH), 5.09 (s, 4H, benzylic), 3.9–4.2 (m, 2H methines), 2.4–2.7 (m, 2H, pseudoequatorial methylenes), 1.8–2.2 (m, 2H pseudoaxial methylenes). Anal. Calcd for C$_{22}$H$_{24}$N$_2$O$_4$: C, 69.46; H, 6.36; N, 7.36. Found: C, 69.24: H, 6.34; N, 7.32.

EXAMPLE 7 trans-4-Cyclohexene-1,2-dicarbonyl Dichloride (21). Freshly distilled fumaryl dichloride (3.7 g; 24 mmol) is dissolved in 10 ml of dry Et$_2$O in an oven dried 20-neck 50 ml round bottom flask, fitted with a gas inlet and dry ice Dewar condenser. The stirred solution is cooled to approximately −50° C. (dry ice/CH$_3$CN). Butadiene (ca. 3 ml) is condensed into the flask and the cooling bath removed. Within 25–30 min the exothermic reaction ceases. After an additional 10 min the excess butadiene and solvent are removed in vacuo to furnish 4.7 g (approx 95%) of the Diels-Alder adduct as a colorless liquid which is used immediately without further purification. IR (neat) 3140 and 1785 cm$^{-1}$.

EXAMPLE 8

Bis(phenylmethyl) trans-4-Cyclohexene-1,2-diyl-bis(carbamate) (22). Trans bis(benzylurethane) 22 is prepared in 94% yield from 16 .2HCl using methodology identical to the one used for the synthesis of the corresponding cis isomer. The white solid obtained after chromatography is recrystallized from toluene:hexane affording fine white needles mp 144°–145° C. IR (K Br) 3320 and 1685 cm$^{-1}$; NMR (90 MHz, CDCl$_3$) δ 7.3 (s, 10H, aromatic), 5.67 (d, 2H, NH, J=2.6 Hz), 5.07 (s, 4H, benzylic), 3.6–3.9 (m, 2H methines), 2.3–2.7 (m, 2H, pseudoequatorial methylenes), 1.8–2.2 (m, 2H, pseudoaxial methylenes). Anal. calc for C$_{22}$H$_{24}$N$_2$O$_4$: C, 69.46; H, 6.36; N, 7.36. Found: C, 69.61; H, 6.27; H, 7.35.

EXAMPLE 9

Bis(phenylmethyl) (1α, 2β, 4α, 5α)-(4,5-Dihydroxy-1,2-cyclohexanediyl)-bis(carbamate) (23). Olefin 22 (2.0 g, 5.3 mmol) is added to a mixture of Me$_2$CO (40 ml), distilled H$_2$O (3 ml) and tBuOH (2 ml). N-methylmorpholine-N-oxide (NMO) monohydrate (0.8 g; 5.9 mmol) and OsO$_4$ (0.009 g; 3.6×10$^{-2}$ mmol) in CCl$_4$ are added, and the reaction is stirred at room temperature under dry argon for 16 h. Me$_2$CO (50 ml) is added, and white precipitate dissolved. Solid NaHSO$_3$ (ca. 0.2 g) is added, and the mixture is stirred for 15 min. The suspension is filtered, and the filtrate is concentrated in vacuo providing a tan solid which is purified on silica gel by eluting with CHCl$_3$:Me$_2$CO 1:1 affording 2.13 g (98%) of white solid mp 172°–173° C. Ir (K Br) 3460 (shoulder), 3320, 1680, 1070 and 1025 cm$^{-1}$; NMR (500 MHz, pyridine-d$_5$) δ 8.40 (d, 1H, aromatic, J=8 Hz), 8.04 (d, 1H, aromatic, J=8 Hz), 7.30–7.40 (m, 4H, aromatic), 7.20–7.30 (m, 4H, aromatic), 6.31 (s, 1H, NH), 6.24 (s, 1H, NH), 5.31 (H$_A$, of A'B' q, 1H, benzylic, J=12.6 Hz, 5.29 (H$_{B'}$ A'B' q, 1H, benzylic, J=12.6 Hz), 5.22 (H$_A$ of AB q, 1H, benzylic, J=12.9 Hz), 5.19 (H$_B$ of AB q, 1H benzylic, J=12.9 Hz), 4.65–4.72 (m, 1H, H-2), 4.35–4.38 (m, 1H, H-4), 4.16–4.26 (m, 1H, H-1), 4.00–4.08 (m, 1H, H-5), 2.63 (deceptively simple d, 1H, H-3a, J=12.5 Hz), 2.48–2.60 (m, 2H, H-6a and H-6e), 1.84 (deceptively simple d, 1H, H-3a, J=12 Hz). Anal. calc for C$_{22}$H$_{26}$N$_2$O$_6$: C, 63.76; H, 6.32; N, 6.76. Found: C, 63.44; H, 6.42; N, 6.62.

EXAMPLE 10

Bis(phenylmethyl) 1α, 2α, 4α, 5α)-(4,5-Dihydroxy-1,2-cyclohexanediyl)-bis(carbamate) (23), and bis(phenylmethyl) (1α, 2α, 4α, 5β)-(4,5-Dihydroxy-1,2-cyclohexanediyl-bix(carbamate) (24). Olefin 20 (2.00 g; 5.3 mmol) is dissolved in 16 ml of Me$_2$CO, 3.2 ml of distilled H$_2$O and 2.1 ml of t-BuOH at room temperature. MNO monohydrate (0.80 g; 5.9 mmol) and OsO$_4$ (0.0091 g; 0.036 mmol) in 0.91 ml of CCl$_4$ are added and stirring is continued under argon for 16 h. Excess OsO$_4$ is decomposed by addition of approximately 0.2 g of NaHSO$_3$. The suspension is stirred for 15–20 min and filtered through MgSO$_4$. The filtrate is concentrated in vacuo affording a tan solid. Chromatography over 120 g of silica gel using $CHCl_3:Me_2CO$ 3:2 as eluant affords 1.14 g (52%) of 24, mp 142°–144° C. and 0.86 g (39%) of 23 mp 157°–158° C. in a ratio of 1.34:1, respectively. For 24 IR (K Br) 3460 (br), 1715, 1680, 1080 and 1020 cm$^{-1}$; NMR (500 MHz, acetone-$d_6$) δ 7.3–7.35 (m, 10H, aromatic), 6.27 (br s, 2H, NH), 5.05 (s, 4H, benzylic), 4.16–4.19 (m, 2H, H$^{-4}$ and H$^{-5}$), 3.95–3.97 (m, 2H, H$^{-1}$ and H$^{-2}$), 3.70 (d, 2H, OH, exch. with $D_2O$, J=3.9 Hz), 1.86–1.97 (m, 4H, methylenes). Anal. calc for $C_{22}H_{26}N_2O_6$: C, 63.76; H, 6.32; N, 6.76. Found: C, 63.55; H, 6.40 ; N, 6.62. For 23 IR (K BR) 3380, 3320, 1710, 1700, 1100 and 1035 cm$^{-1}$ NMR (500 MHz acetone-$d_6$) δ 7.28–7.40 (m, 10H, aromatic), 6.3–6.5 (br s, 2H, NH), 5.06 (s, 4H, benzylic), 4.14 (s, 2H, OH, exch with $D_2O$), 3.8–4.1 (broad m, 4H, methines), 1.9–2.0 (m, 2H, equatorial methylenes), 1.81 deceptively simple d, 2H, axial methylenes, $J_{gem}$=13 Hz). Anal. calc for $C_{22}H_{26}N_2O_6$: C, 63.76; H, 6.32; N, 6.76. Found: C, 63.60; H, 6.33; N, 6.60.

EXAMPLE 11

Bis(phenylmethyl) (1α, 3β, 4β, 6α)-7-Oxabicyclo(4.1.0)heptane-3,4-diylbis(carbamate) (26). Olefin 20 (1.4 g, 3.9 mmol) is dissolved in 15 ml of $CH_2Cl_2$ at room temperature and $NaHCO_3$ (0.31 g; 3.9 mmol) is added. m-Chloroperoxybenzoic acid (freshly purified, 0.63 g; 7.8 mmol) in 10 ml of $CH_2Cl_2$ is added dropwise over 10 min to the vigorously stirred suspension. After 3 h, EtOAc (50 ml) is added, and the solution is washed with 3×15 ml portions of 10% $NaHSO_3$ and 5% $NaHCO_3$ solutions and brine. The organic layer is dried ($Na_2SO_4$) and concentrated in vacuo affording a colorless oil. Four hours following addition of 25 ml of $Et_2O$, colorless needles (1.09) g. are collected by filtration. Flash chromatography of the mother liquor (pet ether:-$Me_2CO$ 3:1) provides an addition 0.18 g of product (mp 107°–108.5° C.) for a combined yield of 1.27 g (86%). IR (K Br) 3420, 3300, 1725, 1690 and 1320 cm$^{-1}$; NMR (500 MHz, CDCl$_3$) δ 7.29–7.35 (m, 10H, aromatic), 5.57 (d, 2H, NH, J=6.4 Hz), 5.10 (H$_A$ of AB q, 2H, benzylic, J=12 Hz), 5.06 (H$_B$ of AB q, 2H, benzylic, J=12 Hz), 3.85 (deceptively simple dd, 2H, H-3 and H-4, J=6 and 13 Hz), 3.21 (s, 2H, H-1 and H-6), 2.35 (deceptively simple d, 2H, H-2e and H-5e, J=13 Hz), 2.02 (dd, 2H, H-2a and H-5a, J=7 and 13 Hz). Anal. Calc for $C_{22}H_{24}N_2O_5$: C, 66.65; H, 6.10; N, 7.07. Found: C, 66.71; H, 6.11; N, 7.21.

EXAMPLE 12

Bis(phenylmethyl) (1α,2α,4β)-(4-Hydroxy-1,2-cyclohexanediyl)-bis(carbamate) (27) and Bis(phenylmethyl) (1α,2α,4α)-4-Hydroxy-1,2-cyclohexanediyl)-bis(carbamate) (28). Olefin 20 (1.5 g, 3.95 mmol) is dissolved in 50 ml of dry THF under argon and cooled in an ice bath. Diborane (1M in THF, 12 ml, 12 mmol) is added dropwise by syringe. After 6 h at 0° C., the reaction is cooled to −20° C. (ice-salt bath). NaOH (12 ml of a 6N solution) and 30% $H_2O_2$ (8 ml) are added cautiously. The reaction is allowed to warm to room temperature over three hours. The aqueous phase is saturated with $K_2CO_3$ and separated from the organic layer. The aqueous solution is extracted with 4×25 ml of $Et_2O$. The combined organic extracts are dried ($Na_2SO_4$) and concentrated in vacuo to yield a thick oil which is purified by flash chromatography ($Et_2O$:-$Me_2CO$; 20:1) affording 0.35 g of 28 and 1.07 g of 27 for a total yield of 91%. Both compounds are obtained as clear oils which solidified after treatment with $Et_2O$/-hexane. For 28: mp 82°–86° C., IR (K Br) 3460 (sh), 3380, 3340, 1695, 1685, 1265, 1070, and 1040 cm$^{-1}$; NMR (500 MHz, CDCl$_3$) δ 7.34 (s, 10H, aromatic), 6.27 (s, 1H, NH), 5.41 (s, 1H, NH), 5.08 (s, 4H, benzylic), 4.00–4.10 (m, 2H), 3.66–3.72 (m, 1H), 1.60–1.92 (m, 6H, methylene). Anal calc for $C_{22}H_{25}N_2O_7$: C, 66.48; H, 6.34; N, 7.05. Found: 66.28; H, 6.50; N, 6.83. For 27: mp 163°–164° C., IR (K Br) 3460 (sh), 3320, 1725, 1700, 1675, 1270, 1245 and 1015 cm$^{-1}$; NMR (500 MHz, CDCl$_3$) δ 7.34 (s, 10H, aromatic), 5.09 (br s, 6H, 2NH and benzylic), 4.15–4.20 (m, 1H, H-4), 3.85–3.91 (m, 2H, H-1 and H-2), 1.4–2.1 (m, 6H, methylene). Anal. calc for $C_{22}H_{25}N_2O_7$: C, 66.48; H, 6.34; N, 7.05. Found: C, 66.46; H, 6.48; N, 6.93.

EXAMPLE 13

Bix(phenylmethyl) (1α,3α,4β,6α)-7-Oxabicyclo(4.1.0)heptane-3,4-diyl-bis(carbamate) (29). Olefin 22 (500 mg, 1.4 mmol) is treated with MCPBA in $NaHCO_3$-buffered $CHCl_3$ for 4 hours at room temperature as described for the preparation of 26. Flash chromatography affords epoxide 29 as a white solid which is recrystallized from $CCl_4$ yielding 380 mg (73%) of fine white needles mp 168°–169° C. IR (K Br) 330, 1685 and 1290 cm$^{-1}$; NMR (500 MHz, CDCl$_3$) δ 7.31 (s, 10H, aromatic), 4.99–5.10 (m, 5H, 4 benzylic and 1 NH), 4.84 (s, 1H, NH), 3.71–3.74 (m, 1H, H-4), 3.53–3.57 (m, 1H, H-3), 3.21 (s, 1H, H-1), 3.13 (deceptively simple t, 1H, H-6, J=4 Hz) 2.55 (deceptively simple dd, 1H, H-5e, J=2, and 15 Hz), 2.46 (deceptively simple dt, 1H, H-2e, J=4, 10 and 15 Hz), 1.83 (deceptively simple dd, 1H, H-2a, J=10 and 15 Hz), 1.74 (ddd, 1H, H-5a, J=2, 10 and 15 Hz). Anal. calc for $C_{22}H_{24}N_2O_5$: C, 66.65; H, 6.10; N, 7.07. Found: C, 66.26; H, 6.16; N, 6.90.

EXAMPLE 14

Bis(phenylmethyl)(1α,2α,4α,5β)-(4,5-Dihydroxy-1,2-cyclohexanediyl)-bis(carbamate) (30). METHOD A: Epoxide 26 (300 mg, 0.76 mmol) is dissolved in 4 ml of THF at room temperature. Two ml of 1% (V/V) aqueous $H_2SO_4$ is added, and the reaction mixture is stirred for 8 hours at room temperature. The solution is diluted with 25 ml of EtOAc and extracted with 2×5 ml portions of 5% $NaHCO_3$ solution and brine. The organic layer is dried ($Na_2SO_4$) and concentrated to an oil that is purified by flash chromatography ($CHCl_3$:$Me_2CO$; 3:2) to furnish 231 mg (74%) of the trans diol as a white solid, mp 141°–142° C. IR (K Br) 3360, 1735, 1680 and 1065 cm$^{-1}$; NMR (500 MHz, pyridine-$d_5$) δ 8.06 (d, 1H, NH, J=8 Hz), 7.95 (br s, 1H, NH), 7.35–7.43 (m, 4H aromatic), 7.22–7.31 (m, 6H, aromatic), 5.12–5.27 (m, 4H, benzylic), 4.51–4.63 (m, 1H, H-4), 4.40–4.51 (m, 1H, H-2), 4.05–4.18 (m, 1H, H-1), 2.41–2.60 (m, 2H, H-3e and H-6e), 2.18–2.30 (m, 1H, H-6a), 2.01–2.16 (m, 1H, H-3a). Anal. calcd for $C_{22}H_{26}N_2O_6$: C, 63.76; H, 6.32; N, 6.76. Found: C, 63.62; H, 6.43; N, 6.58.

METHOD B: Epoxide 26 (300 mg, 0.76 mmol) is dissolved in a mixture of 5 ml of dry THF and 1 ml of distilled deionized $H_2O$. Nafion-H (35-60 mesh powder; 60 mg) is added, and the reaction mixture is heated at reflux with vigorous stirring for 36 hours. The reaction mixture is cooled and the catalyst is removed by filtration. The filtrate is concentrated in vacuo affording a clear oil which is purified as in Method A to furnish 264 mg (84%) of diol 30.

EXAMPLE 15

Bis(phenylmethyl) (1α, 2β, 4α, 5β)-(4,5-Dihydroxy-1,2-cyclohexanediyl)-bis(carbamate) (31) and Phenylmethyl (1α, 5α, 6β, 8β)-(8-Hydroxy-3-oxo-2-oxa-4-azabicyclo[3.3.1]non-6-yl)-carbamate (32). Epoxide 29 (50 mg, 0.13 mmol) is dissolved at room temperature in 1.5 ml of Me$_2$CO with stirring. Aqueous H$_2$SO$_4$ (1% V/V, 0.5 ml) is added, and the solution is stirred at room temperature for two hours. Solid NaHCO$_3$ is added to pH 7 (pH paper). The reaction is concentrated affording a white solid which is purified by preparative tlc (silica gel, 2 developments with CHCl$_3$:Me$_2$CO, 3:2) yielding 6 mg (16%) of the bicyclic 32 mp 214°–215° C. and 36 mg (69%) of diol 31 mp 171°–172° C. For 32, IR (K Br) 3420, 3300, 1735, 1680 and 1065 cm$^{-1}$; NMR (500 MHz, pyridine-d$_5$) δ 8.91 (s, 1H), 7.43 (d, 2H, J=7 Hz), 7.30–7.35 (m, 2H), 7.27 (d, 1H, J=7 Hz), 6.94 (d, 1H, J=7.6 Hz), 5.31 (H$_A$ of AB q, 1H, benzylic, J=12.3 Hz), 5.25 (H$_B$ of AB q, 1H, benzylic, J=12.3 Hz), 4.64–4.70 (m, 1H), 4.32–4.38 (m, 1H), 4.22–4.30 (m, 1H), 3.90–3.96 (m, 1H), 2.71 (deceptively simple doublet, 1H, J=13.8 Hz), 2.32 deceptively simple dt, 1H, J=3.9, 4.5 and 14 Hz), 1.82 (deceptively simple d, 1H, J=15 Hz), 1.74 (deceptively simple d, 1H, H-7a, J=13.8 Hz). Anal. calc for C$_{15}$H$_{18}$N$_2$O$_5$: C, 58.82; H, 5.92; N, 9.15. Found: C, 59.01; H, 5.99; N, 9.07. For 31 IR (K Br) 3360, 3290, 1685 and 1035 cm$^{-1}$; NMR (270 MHz, acetone-d$_6$) δ 7.28–7.33 (m, 10H, aromatic), 6.15 (d, 2H, NH, J=7 Hz), 5.02 (s, 4H, benzylic), 4.01 (d, 2H, OH, exch with D$_2$O, J=3 Hz), 3.80–3.88 (m, 4H, methine), 1.90–1.97 (m, 4H, methylene). Anal. calc for C$_{22}$H$_{26}$N$_2$O$_6$: C, 63.76; H, 6.32; N, 6.76. Found: C, 64.05; H, 6.24; N, 6.65.

EXAMPLE 16

Bis(phenylmethyl) (1α, 2β, 4α, 5α)-(4-Acetyloxy)-5-hydroxy-1,2-cyclohexanediyl)-bis(carbamate) (35) and Diacetate 36. Diol 23 (1.0 g, 2.42 mmol) is dissolved in 50 ml of THF and cooled to −25° C. in dry ice—CCl$_4$. Et$_3$N (0.27 g; 2.4 mmol), DMAP (0.03 g; 0.24 mmol) and Ac$_2$O (0.27 g; 2.66 mmol) are added. After standing for 24 hours in the freezer at −25° C., the solution is concentrated to afford a white solid which is partitioned between EtOAc (100 ml) and 5% HCl solution (20 ml). The organic layer is washed with 20 ml of dilute HCl and 2×20 ml portions of brine and dried (Na$_2$SO$_4$). Concentration furnishes a white solid which is crystallized from CHCl$_3$ to afford 0.61 g of the hydroxy-acetate as a white solid mp 199°–201° C. Flash chromatography (Et$_2$O) of the mother liquor gives 0.095 g (8%) of 36 and another 0.024 g of 35 for a total yield of 74% IR (K Br) 3520, 3310, 1720, 1680, 1265 and 1030 cm$^{-1}$; NMR (500 MHz, pydridine d$_5$) δ 8.55 (s, 1H, aromatic), 8.21 (s, 1H, aromatic), 7.39 (dd, 4H, aromatic, J=7 and 18 Hz), 7.20–7.30 (m, 4H, aromatic), 6.84 (s, 1H, NH), (H$_A$ of AB q, 1H, benzylic, J=12.6 Hz), 5.28 (H$_{A'}$ of A′B′ q, 1H, benzylic, J=12.7 Hz), 5.22 (H$_{B'}$ of A′B′ q, 1H, benzylic, J=12.7 Hz), 5.18 (H$_B$ of AB q, 1H, benzylic, J=12.6 Hz), 5.10 (deceptively simple dt, 1H, H-4, J=5 and 12 Hz), 4.7–4.8 (m, 1H, H-1), 4.50–4.53 (m, 1H, H-5), 4.2–4.3 (m, 1H, H-2), 2.55–2.67 (m, 2H, H-3a and H-6e), 2.40–2.48 (m, 1H, H-3a), 1.80–1.90 (m, 4H, OAc and H-6a). Anal. calc for C$_{24}$H$_{28}$N$_2$O$_7$: C, 63.15; H, 6.18; N, 6.14. Found: C, 62.88; H, 6.24; N, 5.97.

EXAMPLE 17

Bis(phenylmethyl) (1α,2β,4α,5α)-(4,5-Diacetyloxy-1,2-cyclohexanediyl)-bis(carbamate) (36). Diol 23 (350 mg, 0.845 mmol) is dissolved in 20 ml of THF and cooled in an ice bath. Et$_3$N(171 mg; 1.69 mmol), DMAP (21 mg; 0.169 mmol) and Ac$_2$O (345 mg; 3.38 mmol) are added. The reaction is allowed to warm slowly to room temperature. After 22 hours the solution is evaporated to dryness. The residual white solid is dissolved in 25 ml of EtOAc and washed with 2×10 ml portions each of 5% HCl solution and brine. The organic layer is dried (Na$_2$SO$_4$) and concentrated in vacuo to an oil. Upon addition of Et$_2$O (10 ml) and hexane (5 ml), small white rosettes form slowly. After standing for 2 hours, the crystals (349 mg) are collected by filtration. Preparative tlc (Et$_2$O) of the mother liquor affords an additional 40 mg for a total of 392 mg (92%), mp 122°–123° C.; IR (K Br) 3360, 3300, 1740, 1690 and 1250 cm$^{-1}$; NMR (80 MHz, CDCl$_3$) δ 7.29 (s, 10H, aromatic), 4.7–5.3 (m, 8H, benzylic, NH, H-4 and H-5), 3.4–3.9 (m, 2H, H-1 and H-2), 1.5–2.3 (m, 10H, methylene and CH$_3$). Anal. calc for C$_{26}$H$_{30}$N$_2$O$_8$: C, 62.64; H, 6.07; N, 5.62. Found: C, 62.44; H, 6.06; N, 5.40.

EXAMPLE 18

Bis(phenylmethyl) (1α,2β, 4β)-(4-Acetyloxy)-5-oxo-1,2-cyclohexanediyl)-bis(carbamate) (37). The pure hydroxy-acetate 35 (632 mg, 1.38 mmol) is dissolved at room temperature in 40 ml of Me$_2$CO and cooled in an ice bath. Jones reagent (1.7 ml of a solution diluted to 2.5 m in Cr$^{+6}$) is added dropwise. The reaction is stirred for 2 hours at ice bath temperature. Isopropanol is added to destroy the excess oxidant, and the Cr salts are removed by filtration. The filtrate is concentrated to ca. 5 ml in vacuo and partitioned between EtOAc (50 ml) and H$_2$O (10 ml). The organic layer is washed with 10 ml of H$_2$O, 2×10 ml of brine and dried (Na$_2$SO$_4$). Concentration in vacuo affords a white solid which is purified by flash chromatography (CHCl$_3$:Et$_2$O; 1:1) to afford 547 mg (87%) of 37, mp 163°–164° C. IR (K Br) 3350, 3280, 1765, 1720, 1690, 1230, 1060 and 1040 cm$^{-1}$, NMR (500 MHz, CDCl$_3$) δ 7.3 (s, 10H, aromatic), 5.2–5.3 (m, 1H, H-4), 5.0–5.15 (m, 4H, benzylic), 4.0–4.1 (m, 1H, H-2), 3.75–3.85 (m, 1H, H-1), 2.85 (dd, 1H, H-6e, J=3 and 11 Hz), 2.50–2.56 (m, 1H, H-3e), 2.45 (deceptively simple t, 1H, H-6a, J=13 Hz), 2.12 (s, 3H, OAc), 1.72 (deceptively simple q, 1H, H-3a, J=13 and 25 Hz). Anal. calcd. for C$_{24}$H$_{26}$N$_2$O$_7$: C, 63.43; H, 5.77; N, 6.16. Found: C, 63.39; H, 5.82; N, 5.92.

EXAMPLE 19

Bis(phenylmethyl) (1α, 2β, 4β, 5α)-(4,5-Diacetyloxy-1,2-cyclohexanediyl)-bis(carbamate) (38). Keto-acetate 37 (250 mg, 0.551 mmol) is dissolved in THF (8 ml) and absolute EtOH (2 ml) and cooled to −78° C. NaBH$_4$ (total of 12.5 mg; 0.330 mmol) is added in three portions every 10 min. After 1 hour at −78° C., the solution is concentrated in vacuo to furnish a white solid which is partitioned between EtOAc (25 ml), THF (5 ml) and 5 ml of H$_2$O. The organic layer is washed with 5 ml of H$_2$O and dried (Na$_2$SO$_4$). Concentration in vacuo affords a white solid which is dissolved in 10 ml of THF and cooled in an ice bath. Et$_3$N (110 mg; 1.10 mmol), DMAP (13 mg; 0.110 mmol) and Ac$_2$O (168 mg; 1.65 mmol) are added. The reaction is allowed to warm slowly to room temperature, and after 1 hour is concentrated in vacuo to furnish a white solid. CHCl$_3$ (25 ml)

is added, and the solution is washed with 3×5 ml of 5% HCl solution, 2×10 ml of brine, and dried ($Na_2SO_4$). The solvent is removed in vacuo and the white solid crystallized from $CHCl_3/CCl_4$ to provide 135 mg of the product. Preparative tlc ($CHCl_3$:$Et_2O$; 5:1, 2 developments) of the mother liquor furnishes another 30 mg for a total of 165 mg (65%) of 38 mp 220°–221° C.; IR (K Br) 3320, 1730, 1680, 1290, 1250, 1240, 1070 and 1020 $cm^{-1}$; NMR (500 MHz $CDCl_3$) δ 7.31 (s, 10H, aromatic), 5.01–5.09 (m, 6H, 2 NH, and 4 benzylic), 4.89–4.91 (m, 2H, H-4 and H-5), 3.58–3.66 (m, 2H, H-1 and H-2), 2.39 (deceptively simple d, 2H, $H_{3e}$ and $H_{6e}$, J=12 Hz), 2.01 (s, 6H, 2 $OCH_3$), 1.43 (deceptively simple d, 2H, H3a and H6a, J=11 Hz). Anal. calc for $C_{26}H_{30}N_2O_8$: C, 62.64; H, 6.07; N, 5.62. Found: C, 62.82; H, 6.09; H, 5.61.

EXAMPLE 20

Bis(phenylmethyl) (1α, 2β, 4β, 5α)-(4,5-Dihydroxy-1,2-cyclohexanediyl)-bis(carbamate) (39). Diacetate 38 (100 mg, 0.201 mmol) is suspended in 7 ml of MeOH at room temperature. $K_2CO_3$ (61 mg; 0.442 mmol) was added, and the reaction mixture is heated to reflux (diacetate dissolves). After one hour the reaction is cooled to room temperature and stirred for another 1.5 hours. The solvent is removed in vacuo affording a white solid which is recrystallized from $MeOH/H_2O$ affording 65 mg (78%) of diol 39 mp 197°–198° C. IR (K Br) 3400(sh) 3300, 1680, 1280, 1240, 1065 and 1030 $cm^{-1}$; NMR (500 MHz, pyridine $d_5$) δ 8.30 (s, 2H, aromatic), 7.37 (d, 4H, aromatic, J=7.2 Hz), 7.2–7.3 (m, 4H, aromatic), 6.64 (s, 2H, NH), 5.30 ($H_4$ of A B q, 2H, benzylic J=12.6 Hz), 5.21 (H B of A Bq, 2H, benzylic, J=12.8 Hz), 4.19–4.26 (m, 2H, H-4 and H-5), 3.93 (deceptively simple d, 2H, H-1 and H-2, J=9.2 Hz), 2.76 (deceptively simple d, 2H, H-6e and H-3e, J=12.7 Hz), 1.9–2.0 (m, 2H, H-6a and H-3a) anal. calc for $C_{22}H_{26}N_2O_4$: C, 63.76; H, 6.32; N, 6.76. Found: C, 63.84; H, 6.42; H, 6.61.

EXAMPLE 21

Bis(phenylmethyl) (1α, 2β, 4α,)-(4-hydroxy-1,2-cyclohexanediyl) bis(carbamate) (41) and Bis(phenylmethyl) (1α, 2β, 4β)-(4-hydroxy-1,2-cyclohexanediyl) bis(carbamate) (40). Hydroboration-oxidation method. Trans olefin 22 (1.5 g, 3.95 mmol) is treated as described for cis 20. Flash chromatography of the mixture ($Et_2O$: $Me_2CO$; 25:1) afford 0.52 g of 41 and 0.71 g of 40 for a total yield of 78%. For 41: mp 142°–143° C., IR(K Br) 3390, 3280, 1695, 1270, 1120 and 990 $cm^{-1}$; NMR(500 MHz, $CDCl_3$) δ 7.30 (s, 10H, aromatic), 5.30 (d, 1H, NH, J=7.6 Hz), 5.14 (d, 1H, NH, J=7.5 Hz), 5.00–5.12 (m, 4H, benzylic), 4.13–4.18 (m, 1H, $H_4$), 3.84–3.92 (m, 1H, $H_2$), 3.40–3.50 (m, 1H, $H_1$), 2.19 (deceptively simple d, 1H, $H_{3e}$, J=13 Hz), 1.70–1.90 (m, 3H, $H_{5e}$, $H_{6e}$ and $H_{6a}$), 1.53 (deceptively simple t, 1H, $H_{5a}$, J=12 Hz), 1.42 (deceptively simple t, 1H, $H_{3a}$, J=12.6 Hz.) Anal. calc for $C_{22}H_{25}N_2O_7$: C, 66.48; H, 6.34; N, 7.07. Found: C, 66.22; H, 6.58; N, 7.13. For 40: mp 184°–185° C., IR(K Br) 3320, 1680, 1280, 1070 and 1020 $cm^{-1}$; NMR(500 MHz, $CDCl_3$) δ 7.32 (s, 10H, aromatic), 5.00–5.18 (m, 6H, 2NH and benzylic), 3.68–3.76 (m, 1H, $H_4$), 3.45–3.52 (m, 1H, $H_2$), 3.36–3.45 (m, 1H, $H_1$), 2.3 (deceptively simple d, 1H, $H_{3e}$, J=10 Hz), 2.07 (deceptively simple dd, 1H, $H_{5e}$, J=2 and 8 Hz), 1.98 (deceptively simple d, 1H, $H_{5a}$, J=9 Hz), 1.2–1.4 (m, 3H, $H_{6e}$, $H_{3a}$ and $H_{6a}$). Anal. calc for: $C_{22}H_{25}N_2O_7$: C, 66.48; H, 6.34; N, 7.07. Found: C, 66.17; H, 6.34; N, 6.84. $NaBH_4$ reduction method. Ketone 42 (100 mg, 0.263 mmol) is dissolved in 5 ml of absolute ethanol then cooled to −20° C. (dry ice-$CCl_4$). $NaBH_4$ (13 mg; 0.341 mmol) is added in three portions over 30 minutes. After one hour at −20° C., the reaction is concentrated to dryness. The residue is dissolved in 10 ml of EtOAc and washed with 2×5 ml each of $H_2O$ and brine, then dried ($Na_2SO_4$). The mixture is purified by flash chromatography as described above to afford 68 mg of 40 and 7 mg of 41 for a total yield of 72%. *K-Selectride reduction*. Ketone 42 (100 mg, 0.263 mmol) is dissolved in 5 ml of dry THF under argon, and cooled to −78° C. K-Selectride (0.3 ml of a 1M solution in THF) is added dropwise by syringe. After 30 minutes at −78° C., excess hydride is quenched by addition of 20 ml of $Et_2O$ saturated with $H_2O$. The solution is concentrated in vacuo and the residue dissolved in 25 ml of $Et_2O$, and washed with 2×5 ml each of $H_2O$ and brine. The organic layer is dried ($Na_2SO_4$) and concentrated to an oil which is purified as described above, affording 82 mg of 41 and 4 mg of 40 for a total yield of 86%.

EXAMPLE 22

Bis(phenylmethyl) (1α,2β)-(4-oxo-1,2-cyclohexanediyl) bis(carbamate) (42). Alcohol 41 (100 mg, 0.251 mmol) is dissolved in 5 ml of $Me_2CO$ and cooled in an ice bath. Jones reagent (0.3 ml of a 2.5M solution) is added dropwise. After two hours at 0° C., isopropanol is added to quench excess oxidant. The Cr salts are filtered and washed with $Me_2CO$. The blue-green filtrate is concentrated in vacuo to a green and white solid. The residue is partitioned between 25 ml of EtOAc and 10 ml of $H_2O$. The organic layer is washed with 10 ml of $H_2O$, 2×10 ml of brine and dried ($Na_2SO_4$). EtOAc is removed in vacuo to afford a white solid which is recrystallized from $CCl_4$ to afford 87 mg (87%) of the ketone as a white powder mp 135°–136° C., IR(KBr) 3220, 1725, 1685, 1280, 1240 and 1020 $cm^{-1}$; NMR(500 MHz, $CDCl_3$) δ 7.31 (s, 5H, aromatic), 7.30 (s, 5H, aromatic), 5.28 (d, 2H, NH, J=6.1 Hz), 5.00–5.10 (m, 4H, benzylic), 3.75–3.90 (m, 2H, $H_1$ and $H_2$), 2.76 (dd, 1H, $H_{3e}$, J=3.8 and 14.3 Hz), 2.45–2.55 (m, 2H, $H_{5e}$ and $H_{5a}$), 2.34 (deceptively simple t, 1H, $H_{3a}$, J=12.2 Hz), 2.20–2.30 deceptively simple d, 1H, $H_{6e}$, J=7.6 Hz), 1.50–1.60 (m, 1H, $H_{6a}$). Anal. calc for $C_{22}H_{24}N_2O_5$: C, 66.65; H, 6.10; N, 7.07. Found: C, 66.40; H, 6.02; N, 6.86.

EXAMPLE 23

Bis(phenylmethyl) (1α,2α)-(4-oxo-1,2-cyclohexanediyl) bis(carbamate) (43). Alcohol 27 (300 mg, 0.754 mmol) is dissolved in 15 ml of $Me_2CO$ and cooled in an ice bath. Jones reagent (1.5 ml of a 2.5M solution) is added dropwise. After 30 minutes at 0° C., isopropanol is added to destroy excess $Cr^{+6}$, the solids are removed by filtration and washed with $Et_2O$. The blue-green filtrate is concentrated to an oil which is dissolved in 40 ml of $Et_2O$ ml portions each of $H_2O$ and brine. The dried ($Na_2SO_4$) organic layer is reduced in vacuo to a clear oil which is crystallized from $Et_2O$/hexane to afford 281 mg (94%) of 43 as fine white needles mp 105°–106° C., IR(KBr) 3310, 1695, 1260, 1245 and 1090 $cm^{-1}$; NMR(500 MHz, δ 7.30–7.36 (m 10H, aromatic), 5.52 (br s, 1H, NH), 5.08–5.12 (m, 3H, NH and benzylic), 4.30–4.38 (m, 1H, $H_2$), 4.15–4.23 (m, 1H, $H_1$), 2.68–2.78 (m, 1H, $H_{6e}$), 2.43 (dd, 1H, $H_{3e}$, J=5 and 12 Hz), 2.32–2.40 (m, 2H, $H_{5a}$ and $H_{6e}$), 1.82–1.91 (m, 1H, $H_{6a}$). Anal. calc for $C_{22}H_{24}N_2O_5$: C, 66.65; H, 6.10; N, 7.07. Found: C, 66.86; H, 6.00; N, 7.12.

EXAMPLE 24

(SP-4,2-(1α,2α,4α,5α))-dichloro(4,5-dihydroxy-1,2-cyclohexanediamine-N,N')-platinum 44. Diol 25 (100 mg, 0.242 mmol) is added to a suspension of 20 mg 10% Pd/C in 5 ml of MeOH. The Parr bottle is alternatively evacuated (water aspirator) and refilled five times to 20 psi with $H_2$ gas. The suspension is shaken at room temperature for two hours under 20 psi $H_2$. The catalyst is removed by filtration and the filtrate concentrated in vacuo to afford a clear oil. Distilled deionized $H_2O$ (5 ml) is added followed by $K_2PtCl_4$ (100 mg; 0.242 mmol). The flask is swirled to dissolve the salt, stoppered, covered with foil and allowed to stand at room temperature for 24 hours. The yellow-green crystals that form are collected by filtration and recrystallized from $H_2O$ to afford 45 mg (43%) of 44 as small yellow-green cubes. Anal. calc for $C_6H_{14}N_2O_2PtCl_2 \cdot H_2O$: C, 16.75; H, 3.75; N, 6.51; Pt, 45.35; Cl, 16.48. Found: C, 16.39; H, 4.16; N, 6.59; Pt, 44.91; Cl, 16.45.

EXAMPLE 25

(SP-4,2(1α,2α,4β,5β))-dichloro(4,5-dihydroxy-1,2-cyclohexanediamine-N,N')-platinum 45. Diol 24 (100 mg, 0.242 mmol) is treated as described for the synthesis of 44, affording yellow crystals which are recrystallized from $H_2O$-MeOH to deliver 38.7 mg (37%) of 45 as yellow crystals. Anal. calc for $C_6H_{14}N_2O_2PtCl_2 \cdot H_2O$: C, 16.75; H, 3.75; N, 6.51; Pt, 45.35; Cl, 16.48. Found: C, 16.81; H, 3.28; N, 6.54; Pt, 45.21; Cl, 16.75.

EXAMPLE 26

(SP-4,2-(1α, 2β, 4α, 5α))-dichloro(4,5-dihydroxy-1,2-cyclohexanediamine-N, N')-platinum 47. Diol 23 (100 mg, 0.242 mmol) is treated as described for the synthesis for 44. The resulting bright yellow powder is recrystallized from $H_2O$ affording 69 mg (69.5%) of 47 as a bright yellow powder. Anal. calc for $C_6H_{14}N_2O_2PtCl_2 \cdot H_2O$: C, 16.75; H, 3.75; N, 6.51; Pt, 45.35; Cl, 16.48. Found: C, 16.80; H, 3.26; N, 6.45; Pt, 45.49; Cl, 16.35.

EXAMPLE 27

(SP-4,2-(1α, 2β, 4β, 5α))-dichloro(4,5-dihydroxy-1,2-cyclohexanediamine-N, N')-platinum 48. Diol 39 (100 mg, 0.242 mmol) is treated as described for the synthesis of 44. The resulting bright yellow solid is recrystallized from $H_2O$ affording 22 mg (22%) of 48 as small bright yellow needles. Anal. calc for $C_6H_{14}N_2O_2PtCl_2$: C, 17.48; H, 3.42; N, 6.80; Pt, 47.33; Cl, 17.20. Found: C, 17.39; H, 3.31; N, 6.59, Pt, 47.03; Cl, 16.98.

EXAMPLE 28

(SP-4,2-(1α, 2α, 4β))-dichloro(4-hydroxy-1,2-cyclohexanediamine-N,N')-platinum 50. Diol 27 (300 mg, 0.756 mmol) is treated as described for the synthesis of 44. The canary yellow precipitate is filtered and washed with 5% HCl solution, $Me_2CO$ and $Et_2O$, affording 112 mg (37%) of 50 as a yellow powder. Anal calc for $C_6H_{14}N_2OPtCl_2$: C, 18.19; H, 3.56; N, 7.07; Pt, 49.24; Cl, 18.10. Found: C, 17.93; H, 3.72; N, 6.91; Pt, 48.93; Cl, 18.10.

EXAMPLE 29

(SP-4,2-(1α, 2α, 4α))-dichloro(4-hydroxy-1,2-cyclohexanediamine-N,N')-platinum 51. Alcohol 28 (125 mg, 0.314 mmol) is treated as described for the synthesis of 44. After 24 hours the greenish yellow crystals are recrystallized from $H_2O$ affording 46 mg (37%) of 51. Anal calc for $C_6H_{14}N_2OPtCl_2$: C, 18.19; H, 3.56; N, 7.07; Pt, 49.24; Cl, 17.90. Found: C, 18.25; H, 3.62; N, 7.05; Pt, 49.07; Cl, 17.95.

EXAMPLE 30

(SP-4,2-(1α, 2β, 4β))-dichloro(4-hydroxy-1,2-cyclohexanediamine-N,N')-platinum 52. Alcohol 40 (100 mg, 0.252 mmol) is treated as described for the synthesis of 44. The precipitate is collected and recrystallized from $H_2O$ affording 52 as bright yellow needles, 65 mg (65%). Anal calc for $C_6H_{14}N_2OPtCl_2 \cdot \frac{1}{2} H_2O$: C, 17.79; H, 3.73; N, 6.91; Pt, 48.15; Cl, 17.50. Found: C, 17.77; H, 3.85; N, 6.71; Pt, 48.31; Cl, 16.98.

EXAMPLE 31

(SP-4,2-(1α, 2β, 4α))-dichloro(4-hydroxy-1,2-cyclohexanediamine-N,N')-platinum 53. Alcohol 41 (200 mg, 0.503 mmol) is treated as described for the synthesis of 44, affording 99 mg (48%) of 53 as yellow-green needles. Anal. calc for $C_6H_{16}N_2O_2PtCl_2$: C, 17.40; H, 3.89; N, 6.76; Pt, 47.10; Cl, 17.12. Found: C, 17.44; H, 3.82; N, 6.63; pt, 46.68; Cl, 17.38.

EXAMPLE 32

Bis(phenylmethyl) (1α, 2α, 4β, 5β)-(4,5-diacetyloxy-1,2-cyclohexanediyl)bis(carbamate) (55) and Bis(phenylmethyl) (1α, 2α, 4α, 5α)-(4,5-diacetyloxy-1,2-cyclohexanediyl)bis(carbamate) (54). Olefin 20 (1.00 g, 2.6 mmol) is treated with $OsO_4$ and N-methylmorpholine-N-oxide as described for the synthesis of diols 25 and 24. The crude reaction mixture is suspended in ice-cold $CHCl_3$ (40 ml). $Et_3N$ (532 mg; 5.3 mmol), DMAP (96 mg; 0.79 mmol) and $Ac_2O$ (1.074 g; 11 mmol) are added, respectively. The reaction is allowed to warm slowly to room temperature. After 5.5 hours, the solution is washed with 3×10 ml portions each of 5% HCl solution and brine, then dried ($Na_2SO_4$). The solution is concentrated in vacuo and the mixture is purified by flash chromatography ($CHCl_3$:$Et_2O$; 5:1) to afford 320 mg of 54, 356 mg of 55 plus 370 mg of a mixture for a total of 1.046 g (80%). For 54: mp 84°-86° C., IR(K Br) 3300, 1730, 1705, 1250, 1235, 1055 and 1030 $cm^{-1}$; NMR(90 MHz, $CDCl_3$) δ 7.34 (s, 10H, aromatic), 5.0-5.2 (m, 8H, benzylic, NH, $H_4$ and $H_5$), 4.0-4.3 (m, 2H, $H_1$ and $H_2$), 1.7-2.1 (m, 10H, methylene and 2 $CH_3$). For 55: mp 129°-130° C., IR(K Br) 3300, 1730, 1690, 1245, 1055 and 1020 $cm^{-1}$; NMR(90 MHz, $CDCl_3$) 7.33 (s, 10H, aromatic), 5.0-5.5 (m, 8H, benzylic, NH, $H_4$ and $H_5$), 3.9-4.1 (m, 2H, $H_1$ and $H_2$) 1.8-2.1 (m, 10H, methylene and 2$CH_3$). Anal. (of mixture) calc for: $C_{26}H_{30}N_2O_8$: C, 62.64; H, 6.07; N, 5.62. Found: C, 62.37; H, 6.21; N, 5.40.

EXAMPLE 33

(SP-4,2-(1α,2α,4α,5α))-dichloro(4,5-diacetyloxy-1,2-cyclohexanediamine-N,N')-platinum 57. Diacetate 54 (100 mg, 0.201 mmol) is added to a suspension of 10% Pd/C in 5 ml of MeOH. The bottle is alternatively avacuated (water aspirator) and refilled to 20 psi with $H_2$ gas. The suspension is shaken under 20 psi of $H_2$ for two hours at room temperature. The catalyst is filtered and the filtrate concentrated in vacuo to afford a clear oil. The residue is dissolved in 5 ml of distilled deionized $H_2O$ and $K_2PtCl_4$ (83 mg; 0.201 mmol) is added. The flask is swirled to dissolve the salt, stoppered and covered with foil. After standing at room temperature for 24 hours, the yellow precipitate is filtered and washed with 5% HCl solution, $Me_2CO$ and $Et_2O$ to afford 64 mg (65%) of 57. Anal. calc for $C_{10}H_{18}N_2O_4PtCl_2$: C, 24.20; H, 3.66; N, 5.64; Pt, 39.31; Cl, 14.29. Found: C, 24.33; H, 3.69; N, 5.50; Pt, 39.11; Cl, 13.94.

EXAMPLE 34

(SP-4,2-(1α,2α,4β,5β))-dichloro(4,5-diacetyloxy-1,2-cyclohexanediamine-N,N')-platinum 56. Diacetate 55 (100 mg, 0.201 mmol) is treated as described for the synthesis of 57. The brown precipitate is washed with 5% HCl solution, Me$_2$CO and Et$_2$O to afford 49 mg (49%) of 56. Anal calc for $C_{10}H_{18}N_2O_4PtCl_2$: C, 24.20; H, 3.66; N, 5.64; Pt, 39.31; Cl, 14.29. Found: C, 23.98; H, 3.79; H, 5.50; Pt, 39.98; Cl, 13.94.

EXAMPLE 35

(SP-4,2-(1α,2β,4α,5α))-dichloro(4,5-diacetyloxy-1,2-cyclohexanediamine-N,N')-platinum 58. Diacetate 36 (100 mg, 0.201 mmol) is treated as described for the synthesis of 57. The bright yellow precipitate is washed with 5% HCl solution, Me$_2$CO and Et$_2$O to afford 73 mg (73%) of 58 as a bright yellow powder. Anal calc for $C_{10}H_{18}N_2O_4PtCl_2$: C, 24.20; H, 3.66; N, 5.64; Pt, 39.31; Cl, 14.29. Found: C, 24.46; H, 3.75; N, 5.58; Pt, 39.03; Cl, 13.37.

We claim:

1. A process for preparing a diastereomeric SP-1,2-dihydroxylated-4,5-diaminocylohexane compound which comprises the steps: dihydroxylating a bis(benzylcarbamate) (Cbz) compound of either one of the formula

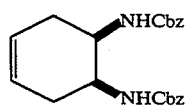  I and

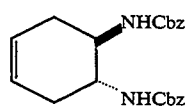  II to give the corresponding dihydroxylated benzylcarbamate-protected diamine compound of one of the formula

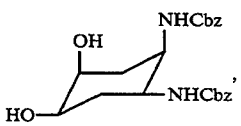  IIIa

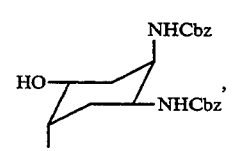  IIIb

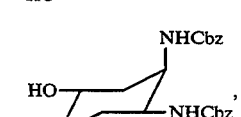  IIIc

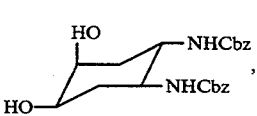  IIId

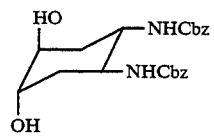  IIIe and

  IIIf and thereafter liberating, by catalytic hydrogenation, said diastereomeric 1,2-dihydroxylated-4,5-diaminocyclohexane compound of one of the formulae:

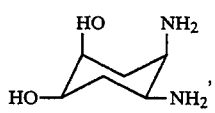  IVa

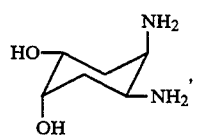  IVb

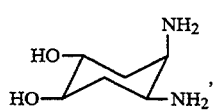  IVc

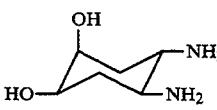  IVd

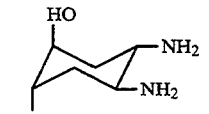  IVe and

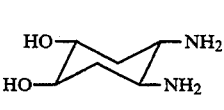  IVf wherein said diastereomeric 1,2-dihydroxylated-4,5-diaminocyclohexane compound of one of the formulae IVa, IVb, IVc, IVd, IVe and IVf immediately after hydrogenation is platinated to form a SP-4,2-dichloro(4,5-dihydroxy-1,2-cyclohexanediamine-N, N')-platinum compound of one of the formulae, respectively

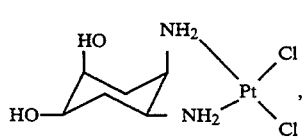  Xa

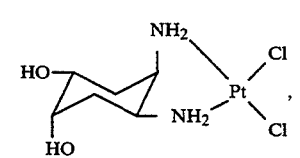  Xb

-continued

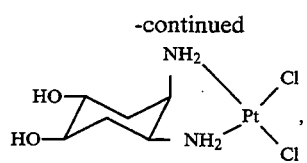 Xc

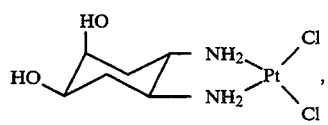 Xd

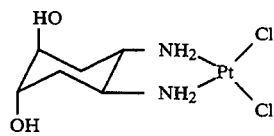 Xe and

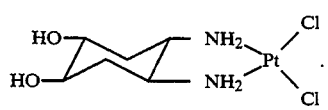 Xf

2. A process according to claim 1, wherein said bis(benzylcarbamate) compound of the formula

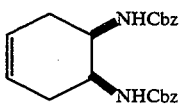 I is dihydroxylated by catalytic osmylation to give a diastereomeric mixture of said dihydroxylated Cbz-protected diamine compounds of the formulae IIIa and IIIb, which serve as precursors to said cis-syn-cis compound, IVa and said cis-anti-cis compound, IVb, 1,2-dihydroxylated-4,5-diaminocyclohexane compounds; wherein said bis(benzylcarbamate) compound of the formula I above prior to said step of catalytic hydrogenation, is catalytically esterified to give compounds of the formulae, respectively,

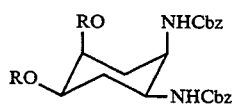 XIa

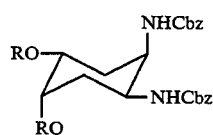 XIb wherein R is an ester, or organic acetate, group having from 2 to 22 carbon atoms and following said step of catalytic hydrogenation, platinating said compounds of the formula XIa and XIb to give corresponding compounds of the formulae, respectively,

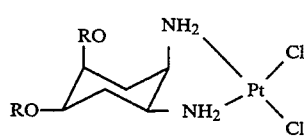 XIIa

-continued

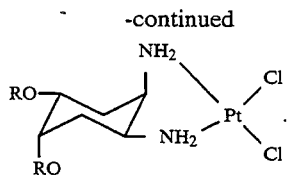 XIIb

3. A process according to claim 2, wherein said bis compound of the formula

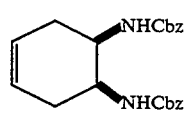 I prior to said step of catalytic hydrogenation, is catalytically acetylated to give compounds of the formulae, wherein Ac is an acetyl group:

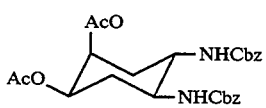 XIa

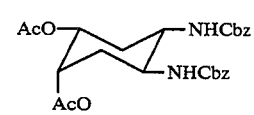 XIb and, following said step of catalytic hydrogenation, platinating said compounds of the formulae to give corresponding SP-4,2-dichloro(4,5-diacetyloxy-1,2-cyclohexanediamine-N,N')-platinum compounds of the formulae, respectively;

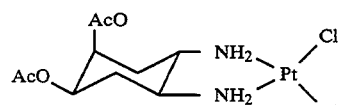 XIIa

 XIIb

4. A process according to claim 1, wherein said bis(benzylcarbamate) compound of the formula II is dihydroxylated by catalytic osmylation to give said dihydoxylated Cbz-protected diamine compound of the formula IIId, which serves as the precursor to said cis-anti-trans, IVd, 1,2-dihydoxylated-4,5-diamino cyclohexane-compound of the formula IVd; wherein said dihydroxylated Cbz-protected diamine compound of the formula

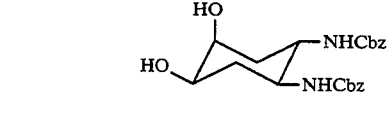 IIId prior to said step of catalytic hydrogenation is catalytically esterified to give a compound of the formula

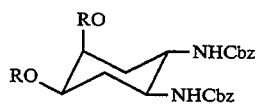   XIc wherein R is an ester, or organic acetate, group having from 2 to 22 carbon atoms and following said step of catalytic hydrogenation, platinating said compound of the formula XIc to give a corresponding compound of the formula

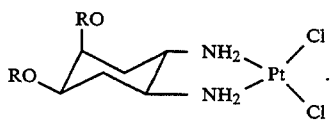   XIIc

5. A process according to claim 4, wherein said dihydroxylated Cbz-protected diamine compound of the formula

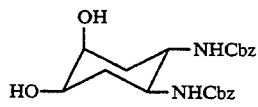   IIId prior to said step of catalytic hydrogenation, is catalytically acetylated to give a compound of the formula, wherein Ac is an acetyl group:

   XIc and following said step of catalytic hydrogenation, platinating said compound of the formula XIc to give the corresponding SP-4,2-dichloro(4,5-diacetyloxy-1,2-cyclohexanediamine-N,N')-platinum compound of the formula:

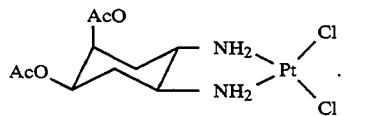   XIIc

6. A process for preparing a diastereomeric SP-4,2-dichloro(4-hydroxy-1,2-cyclohexanediame-N,N')-platinum compound which comprises the steps of monohydroxylating a bis compound of one of the formula:

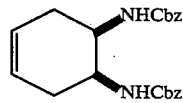   I and

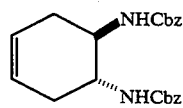   II to give a corresponding monohydroxylated benzylcarbamate-protected diamine compound of one of the formula, respectively,

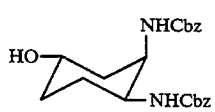   XIIIa

   XIIIb

   XIIIc

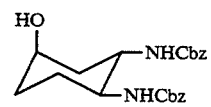   XIIId catalytically hydrogenating and therafter platinating to give said corresponding diastereomeric SP-4,2-dichloro(4-hydroxy-1,2-cyclohexanediamine N,N')-platinum compound of one of the formulae:

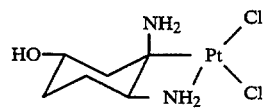   XIVa

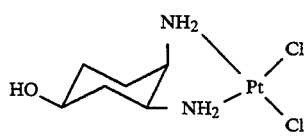   XIVb

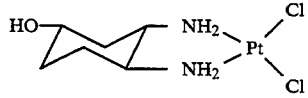   XIVc

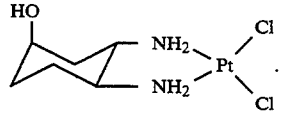   XIVd

* * * * *

UNITED STATES PATENT AND TRADEMARK OFFICE
CERTIFICATE OF CORRECTION

PATENT NO.  : 5,336,796
DATED       : August 9, 1994
INVENTOR(S) : Donald T. Witiak and David P. Rotella It is certified that error appears in the above—identified patent and that said Letters Patent is hereby corrected as shown below:

In column 11, Table I, last column heading, please delete "H6a" and insert --H6e--.

In column 11, Table I, last column entitled H6e, last row entitled 4f, please delete "3.02" and insert --2.02--.

In column 13, line 12, Scheme 4a, after the number 32, please insert --(16%)--.

In column 17, line 44, please delete "4a-4a" and insert --4a-4f--.

In column 18, Table IV, in the column entitled pt complex, after the number 52, please insert --st--.

In column 24, line 24, after 6.27; please delete "H" and insert --N--.

UNITED STATES PATENT AND TRADEMARK OFFICE
CERTIFICATE OF CORRECTION

PATENT NO. : 5,336,796
DATED : August 9, 1994
INVENTOR(S) : Donald T. Witiak and David P. Rotella It is certified that error appears in the above-indentified patent and that said Letters Patent is hereby corrected as shown below:

In column 24, line 60, after cyclohexanediyl-, please delete "bix" and insert --bis--.

Signed and Sealed this

Eighteenth Day of April, 1995

Attest:

BRUCE LEHMAN

Attesting Officer

Commissioner of Patents and Trademarks